(12) United States Patent
Modlin et al.

(10) Patent No.: US 6,466,316 B2
(45) Date of Patent: *Oct. 15, 2002

(54) APPARATUS AND METHODS FOR SPECTROSCOPIC MEASUREMENTS

(75) Inventors: Douglas N. Modlin, Palo Alto, CA (US); Jon F. Petersen, Redwood City, CA (US); John C Owicki, Palo Alto, CA (US)

(73) Assignee: LJL BioSystems, Inc., Sunnyvale, CA (US)

( * ) Notice: Subject to any disclaimer, the term of this patent is extended or adjusted under 35 U.S.C. 154(b) by 0 days.

(21) Appl. No.: 09/765,869

(22) Filed: Jan. 19, 2001

(65) Prior Publication Data

US 2001/0007496 A1 Jul. 12, 2001

Related U.S. Application Data

(63) Continuation of application No. PCT/US99/16621, filed on Jul. 23, 1999.
(60) Provisional application No. 60/094,275, filed on Jul. 27, 1998, provisional application No. 60/117,278, filed on Jan. 26, 1999, and provisional application No. 60/136,566, filed on May 28, 1999.

(51) Int. Cl.$^7$ .............................................. G01N 21/64
(52) U.S. Cl. ..................... 356/318; 250/458.1; 356/73; 356/417
(58) Field of Search ................................ 356/318, 317, 356/417, 73; 250/458.1, 459.1, 461.1; 422/82.08; 436/172

(56) References Cited

U.S. PATENT DOCUMENTS

| | | | |
|---|---|---|---|
| 2,719,214 A | 9/1955 | Potter | |
| 3,013,467 A | 12/1961 | Minsky | |
| 3,423,581 A | 1/1969 | Baer | |
| 3,516,736 A | 6/1970 | Weaver | |
| 5,319,436 A | 6/1974 | Manns et al. | |
| 3,849,654 A | 11/1974 | Malvin | |
| 3,885,162 A | 5/1975 | Geertz | |
| 3,932,023 A | 1/1976 | Humer | |
| 4,011,451 A | 3/1977 | Nelson | |
| 4,067,653 A | 1/1978 | Fletcher et al. | |
| 4,074,939 A | 2/1978 | Rabl | |
| 4,076,420 A | 2/1978 | De Maeyer et al. | |
| 4,100,416 A | 7/1978 | Hirschfeld | |
| 4,144,452 A | 3/1979 | Harte | |
| 4,150,870 A | 4/1979 | d'Auria | |
| 4,203,670 A | 5/1980 | Bromberg | |
| 4,240,751 A | 12/1980 | Linnecke et al. | |
| 4,296,326 A | 10/1981 | Halsop et al. | |
| 4,451,149 A | 5/1984 | Noeller | |
| 4,451,433 A | 5/1984 | Yamashita et al. | |
| 4,485,430 A | 11/1984 | Achiaga Fustel | |
| 4,501,970 A | * | 2/1985 | Nelson |

(List continued on next page.)

FOREIGN PATENT DOCUMENTS

| | | |
|---|---|---|
| EP | 0 222 341 A1 | 5/1987 |
| EP | 0 266 881 A2 | 11/1988 |

(List continued on next page.)

OTHER PUBLICATIONS

*Standard Handbook for Electrical Engineers*, Donald G. Fink and H. Wayne Beaty, pp. 22–2 through 22–5, 11$^{th}$ ed., 1978.

(List continued on next page.)

*Primary Examiner*—F. L. Evans
*Assistant Examiner*—Layla Lauchman
(74) *Attorney, Agent, or Firm*—Kolisch Hartwell PC

(57) ABSTRACT

Apparatus and methods for measuring light transmitted from a sample. The apparatus may include a stage, a light source, and a detector. The stage may be configured to hold a microplate having a plurality of sample wells. The apparatus may be configured to take measurements of one or more of absorbance, scattering, reflectance and luminescence. The apparatus may permit simultaneous measurements of two or more of these properties.

34 Claims, 11 Drawing Sheets

U.S. PATENT DOCUMENTS

| | | | |
|---|---|---|---|
| 4,567,847 A | * 2/1986 | Linner | |
| 4,626,684 A | * 2/1986 | Landa | |
| 4,591,550 A | * 5/1986 | Hafeman et al. | |
| 4,646,214 A | * 2/1987 | Mendleski | |
| 4,685,801 A | * 8/1987 | Minekane | |
| 4,699,512 A | * 10/1987 | Koshi | |
| 4,704,255 A | * 11/1987 | Jolley | |
| 4,707,067 A | * 11/1987 | Haberland et al. | |
| 4,730,921 A | * 3/1988 | Klein et al. | |
| 4,737,464 A | * 4/1988 | McConnel et al. | |
| 4,738,825 A | * 4/1988 | Kelln et al. | |
| 4,741,619 A | * 5/1988 | Humphries et al. | |
| 4,753,501 A | * 6/1988 | Battle | |
| 4,758,786 A | * 7/1988 | Hafeman | |
| 4,762,420 A | * 8/1988 | Bowley | |
| 4,772,453 A | * 9/1988 | Lisenbee | |
| 4,784,275 A | * 11/1988 | Fridge | |
| 4,802,768 A | * 2/1989 | Gifford et al. | |
| 4,808,828 A | * 2/1989 | Kitamori et al. | |
| 4,810,096 A | * 3/1989 | Russel et al. | |
| 4,826,660 A | 5/1989 | Smith et al. | |
| 4,855,930 A | 8/1989 | Chao et al. | |
| 4,868,103 A | 9/1989 | Stavrianopoulos et al. | |
| 4,873,633 A | 10/1989 | Mezei et al. | |
| 4,877,965 A | 10/1989 | Dandliker et al. | |
| 4,885,087 A | 12/1989 | Kopf | |
| 4,892,409 A | 1/1990 | Smith | |
| 4,897,548 A | 1/1990 | Döme et al. | |
| 4,923,819 A | 5/1990 | Fernandez et al. | |
| 4,931,402 A | 6/1990 | Abplanalp | |
| 4,936,682 A | 6/1990 | Hoyt | |
| 4,948,442 A | 8/1990 | Manns | |
| 4,963,815 A | 10/1990 | Hafeman | |
| 4,968,148 A | 11/1990 | Chow et al. | |
| 4,979,821 A | 12/1990 | Schutt et al. | |
| 5,009,488 A | 4/1991 | Fay et al. | |
| 5,018,866 A | 5/1991 | Osten | |
| 5,020,995 A | 6/1991 | Levy | |
| 5,034,613 A | 7/1991 | Denk et al. | |
| 5,039,219 A | 8/1991 | James et al. | |
| 5,047,215 A | 9/1991 | Manns | |
| 5,058,045 A | 10/1991 | Ma | |
| 5,082,628 A | 1/1992 | Andreotti et al. | |
| 5,084,246 A | 1/1992 | Lyman et al. | |
| 5,091,652 A | 2/1992 | Mathies et al. | |
| 5,095,517 A | 3/1992 | Monguzzi et al. | |
| 5,096,807 A | 3/1992 | Leaback | |
| 5,164,319 A | 11/1992 | Hafeman et al. | |
| 5,169,601 A | 12/1992 | Ohta et al. | |
| 5,192,510 A | 3/1993 | Zoha et al. | |
| 5,196,709 A | 3/1993 | Berndt et al. | |
| 5,198,670 A | 3/1993 | VanCauter et al. | |
| 5,206,568 A | 4/1993 | Björnson et al. | |
| 5,208,161 A | 5/1993 | Saunders et al. | |
| 5,208,651 A | 5/1993 | Buican | |
| 5,216,488 A | 6/1993 | Tuunanen et al. | |
| 5,225,164 A | 7/1993 | Astle | |
| 4,397,560 A | 8/1993 | Andreson | |
| 5,257,202 A | 10/1993 | Feddersen et al. | |
| 5,270,788 A | 12/1993 | Cercek et al. | |
| 5,273,718 A | 12/1993 | Sköld et al. | |
| 5,275,951 A | 1/1994 | Chow et al. | |
| 5,281,825 A | 1/1994 | Berndt et al. | |
| 5,289,407 A | 2/1994 | Strickler et al. | |
| 5,307,144 A | 4/1994 | Hiroshi et al. | |
| 5,315,015 A | 5/1994 | Hui et al. | |
| 5,317,485 A | 5/1994 | Merjanian | |
| 5,323,008 A | 6/1994 | Studholme et al. | |
| 5,323,010 A | 6/1994 | Gratton et al. | |
| 5,340,716 A | 8/1994 | Ullman et al. | |
| 5,340,747 A | 8/1994 | Eden | |
| 5,341,215 A | 8/1994 | Seher | |
| 5,353,112 A | 10/1994 | Smith | |
| 5,355,215 A | 10/1994 | Schroeder et al. | |
| 5,357,095 A | 10/1994 | Weyrauch et al. | |
| 5,361,626 A | 11/1994 | Colligan et al. | |
| 5,384,093 A | 1/1995 | Ootani et al. | |
| 5,401,465 A | 3/1995 | Smethers et al. | |
| 5,418,371 A | 5/1995 | Aslund et al. | |
| 5,420,408 A | 5/1995 | Weyrauch et al. | |
| 5,436,718 A | 7/1995 | Fernandes et al. | |
| 5,445,935 A | 8/1995 | Royer | |
| 5,449,921 A | 9/1995 | Baba | |
| 5,457,527 A | 10/1995 | Manns et al. | |
| 5,459,300 A | 10/1995 | Kasman | |
| 5,480,804 A | 1/1996 | Niwa et al. | |
| 5,485,530 A | 1/1996 | Lakowicz et al. | |
| 5,487,872 A | 1/1996 | Hafeman et al. | |
| 5,491,343 A | 2/1996 | Brooker | |
| 5,500,188 A | 3/1996 | Hafeman et al. | |
| 5,504,337 A | 4/1996 | Lakowicz et al. | |
| 5,512,492 A | 4/1996 | Herron et al. | |
| 5,523,573 A | 6/1996 | Hänninen et al. | |
| 5,527,684 A | 6/1996 | Mabile et al. | |
| 5,528,046 A | 6/1996 | Ishikawa | |
| 5,528,050 A | * 6/1996 | Miller et al. | 250/585 |
| 5,537,343 A | 7/1996 | Kikinis et al. | |
| 5,541,113 A | 7/1996 | Siddigi et al. | |
| 5,542,012 A | 7/1996 | Fernandes et al. | |
| 5,557,398 A | 9/1996 | Wechsler et al. | |
| 5,561,068 A | 10/1996 | Rounbehler et al. | |
| 5,589,136 A | 12/1996 | Northrup et al. | |
| 5,589,350 A | 12/1996 | Bochner | |
| 5,589,351 A | 12/1996 | Harootunian | |
| 5,592,289 A | 1/1997 | Norris | |
| 5,593,867 A | 1/1997 | Walker et al. | |
| 5,595,710 A | 1/1997 | Van Dusen et al. | |
| 5,599,500 A | 2/1997 | Jones | |
| 5,604,130 A | 2/1997 | Warner et al. | |
| 5,620,894 A | 4/1997 | Barger et al. | |
| 5,626,134 A | 5/1997 | Zuckerman | |
| 5,631,734 A | 5/1997 | Stern et al. | |
| 5,633,724 A | 5/1997 | King et al. | |
| 5,635,402 A | 6/1997 | Alfano et al. | |
| 5,641,633 A | 6/1997 | Linn et al. | |
| 5,645,800 A | 7/1997 | Masterson et al. | |
| 5,663,545 A | 9/1997 | Marquiss | |
| 5,670,113 A | 9/1997 | Akong et al. | |
| 5,672,880 A | 9/1997 | Kain | |
| 5,676,943 A | 10/1997 | Baetge et al. | |
| 5,677,196 A | 10/1997 | Herron et al. | |
| 5,679,310 A | 10/1997 | Manns | |
| 5,736,410 A | 4/1998 | Zarling et al. | |
| 5,738,825 A | 4/1998 | Rudigier et al. | |
| 5,741,554 A | 4/1998 | Tisone | |
| 5,746,974 A | 5/1998 | Massey et al. | |
| 5,750,410 A | 5/1998 | Dou et al. | |
| 5,756,292 A | 5/1998 | Royer | |
| 5,766,875 A | 6/1998 | Hafeman et al. | |
| 5,780,857 A | 7/1998 | Harju et al. | |
| 5,784,152 A | * 7/1998 | Heffelfinger et al. | 356/73 |
| 5,798,083 A | 8/1998 | Massey et al. | |
| 5,798,085 A | 8/1998 | Seaton et al. | |
| 5,825,617 A | 10/1998 | Kochis et al. | |
| 5,842,582 A | 12/1998 | DeStefano, Jr. | |
| 5,888,454 A | 3/1999 | Leistner et al. | |
| 5,905,571 A | 5/1999 | Butler et al. | |
| 5,933,232 A | 8/1999 | Atzler et al. | |
| 5,959,738 A | 9/1999 | Hafeman et al. | |
| 5,989,835 A | 11/1999 | Dunlay et al. | |
| 5,993,746 A | 11/1999 | Priha et al. | |

| | | | |
|---|---|---|---|
| 6,020,591 A | | 2/2000 | Harter et al. |
| 6,025,985 A | | 2/2000 | Leytes et al. |
| 6,033,100 A | | 3/2000 | Marquiss et al. |
| 6,071,748 A | | 6/2000 | Modlin et al. |
| 6,097,025 A | | 8/2000 | Modlin et al. |
| 6,137,108 A | * | 10/2000 | DeThomas et al. ..... 250/339.07 |
| 6,137,584 A | | 10/2000 | Seidel et al. |
| 6,159,425 A | | 12/2000 | Edwards et al. |
| 6,187,267 B1 | | 2/2001 | Taylor et al. |
| 6,236,456 B1 | * | 5/2001 | Giebeler et al. ............... 356/18 |

FOREIGN PATENT DOCUMENTS

| | | |
|---|---|---|
| EP | 0 977 037 A1 | 7/1999 |
| EP | 0 993 916 A2 | 10/1999 |
| EP | 0 995 555 A1 | 10/1999 |
| EP | 1 003 020 A1 | 5/2000 |
| EP | 1 003 039 A1 | 5/2000 |
| GB | 2228081 | 8/1990 |
| GB | 2215838 | 9/1990 |
| WO | WO99/04288 | 1/1999 |
| WO | WO99/08233 | 2/1999 |
| WO | WO99/23466 | 5/1999 |
| WO | WO99/37203 | 7/1999 |
| WO | WO99/42817 | 8/1999 |
| WO | WO99/54711 | 10/1999 |
| WO | WO00/04364 | 1/2000 |
| WO | WO00/06989 | 2/2000 |
| WO | WO00/06990 | 2/2000 |
| WO | WO00/06991 | 2/2000 |
| WO | WO00/42209 | 7/2000 |
| WO | WO00/50877 | 8/2000 |
| WO | WO00/55372 | 9/2000 |
| WO | WO00/66269 | 11/2000 |
| WO | WO01/04608 | 1/2001 |

OTHER PUBLICATIONS

*Fundamentals of Light Microscopy*, Spencer, Cambridge University Press, 1982.

Joseph R. Lakowicz, *Principles of Fluorescence Spectroscopy*, First Edition, Sep. 1983.

*Basic Fluorescence Microscopy*, Taylor et al., *Methods in Cell Biology*, vol. 29, pp. 207–237, 1989.

*Quantitative Fluorescence Microscopy Using Photomultiplier Tubes and Imaging Detectors*, Wampler et al., *Methods in Cell Biology*, vol. 30, pp. 239–267, 1989.

*Three–Dimensional Confocal Fluorescence Microscopy*, Brakenhoff et al., *Methods in Cell Biology*, vol. 30, pp. 379–389, 1989.

*Laser Scanning Confocal Microscopy of Living Cells*, Lemasters et al., *Optical Microscopy: Emerging Methods and Applications*, pp. 339–345, 1993.

*Time–Resolved Fluorescence Lifetime Imaging*, vande Ven et al., *Optical Microscopy: Emerging Methods and Applications*, pp. 373–389, 1993.

*Electrochemiluminescence: A New Diagnostic and Research Tool*, Yang et al., *Bio/Technology*, vol. 12, pp. 193–194, Feb. 1994.

*Sorting Single Molecules: Application to Diagnostics and Evolutionary Biotechnology*, Eigen et al., *PNAS*, vol. 91, pp. 5740–5747, 1994.

*High Throughput Screening Using Dynamic Fluorescence*, Swift et al., *SPIE*, vol. 2388, pp. 182–189, Feb. 6–8, 1995.

Genesis Series Robotic Sample Processors brochure, Tecan AG, Oct. 1997.

Genesis Robotic Microprocessor brochure, Tecan AG, Nov. 1997.

A Measure of Brilliance, TR717 Microplate Luminometer brochure, Tropix, Inc., 1997.

Advanced Microplate Detection Systems brochure, Tecan AG, Feb. 1998.

The SPECTRA Family brochure, Tecan AG, Feb. 1998.

Assist Plate Handling Device brochure, Labsystems, May 1998.

Wallac Time–Resolved Fluorometry—The Key to Improved Assay Sensitivity, internet description pages, Jul. 7, 1998.

Wallac 1234 DELFIA Fluorometer Counter, internet description page, Jul. 7, 1998.

Wallac 1420 VICTOR Multilabel Counter, internet description pages, Jul. 7,, 1998.

Wallac 1420 VICTOR$^2$ Multilabel Counter, internet description pages, Jul. 7, 1998.

Wallac 1442 ARTHUR Multi–Wavelength Fluoroimager, internet description page, Jul. 7, 1998.

Wallac Labeling Reagents for Time–Resolved Fluorometry, internet description pages, Jul. 7, 1998.

Genesis Assay Workstation brochure, Tecan AG, Jul. 1998.

Genesis Logistics Workstation brochure, Tecan AG, Jul. 1998.

Polarion brochure, Tecan AG, Aug. 1998.

CytoFluor Fluorescence Multi–Well Plate Reader brochure, PerSeptive Biosystems, 1998.

Microplate Instrumentation Catalogue 1998, Labsystems, 1998.

*Fixed Polarizer Ellipsometry for Simple and Sensitive Detection of Thin Films Generated by Specific Molecular Interactions: Applications in Immunoassays and DNA Sequence Detection*, Ostroff et al., *Clinical Chemistry*, 44:9, pp. 2031–2035, 1998.

Magellan, Instrument Control and Data Analysis Software brochure, Tecan AG, Nov. 1999.

TWISTER™, Tecan's Automated Microplate Handler brochure, Tecan AG, Nov. 1999.

*A Microfabricated Fluorescence–Activated Cell Sorter*, Fu et al., *Nature Biotechnology*, vol. 17, pp. 1109–1111, Nov. 1999.

Absorbance Readers brochure, Tecan AG, Dec. 1999.

ULTRA—The Solution for HTS and Assay Development brochure, Tecan Austria GMBH, Dec. 1999.

*Principles of Fluorescence Spectroscopy*, Joseph R. Lakowicz, Second Edition, 1999.

CyBi™–Lumax 1,536 brochure, CyBio AG, May 2000.

CyBi™–PlateSafe brochure, CyBio AG, May 2000.

SPECTRAmax® GEMINI XS brochure, Molecular Devices Corp., Jun. 2000.

SPECTRAmax® PLUS$^{384}$ brochure, Molecular Devices Corp., Jun. 2000.

Packard BioScience Company Introduces the Fusion™ Universal Microplate Analyzer press release, Packard BioScience Company, Jun. 29, 2000.

Labcyte: Research and Clinical Instruments for Life Sciences brochure, Arlena Research LLC, Aug. 1, 2000.

Fusion™ Universal Microplate Analyzer, Packard BioScience Company, Aug. 2000.

CyBi™–Screen–Machine: One System–Many Solutions brochure, CyBio AG, 2000.

Acumen Explorer brochure, Acumen, undated.

FLIPR 384: Essential Technology for Drug Discovery brochure, Molecular Devices Corp., undated.

FLUOstar Galaxy brochure, BMG Labtechnologies GmbH, undated.

NEPHELOstar brochure, BMG Labtechnologies GmbH, undated.

LUMIstar Galaxy brochure, BMG Labtechnologies GmbH, undated.

POLARstar Galaxy brochure, BMG Labtechnologies GmbH, undated.

POLARstar Galaxy flyer, BMG Labtechnologies GmbH, undated.

* cited by examiner

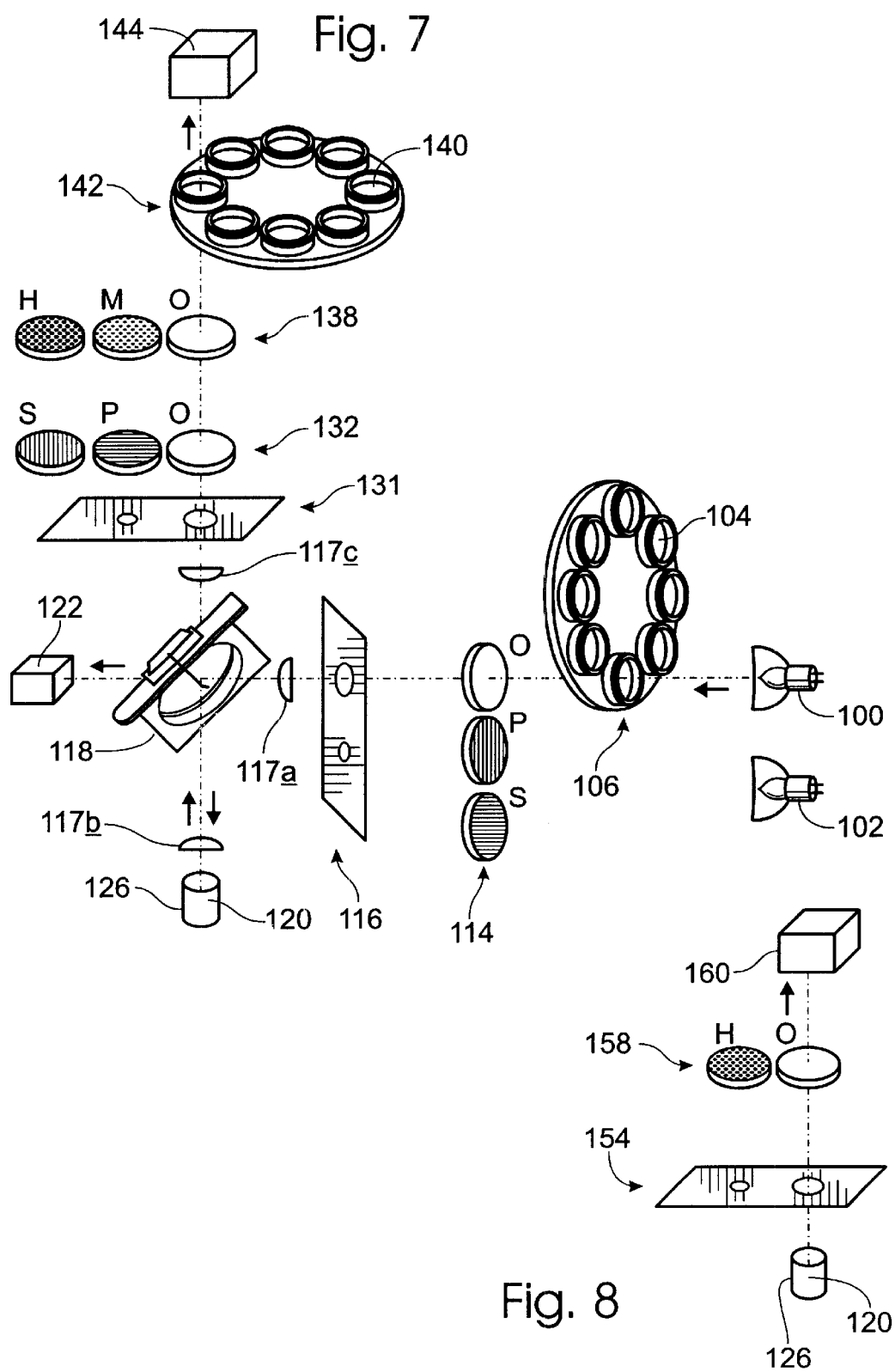

APPARATUS AND METHODS FOR SPECTROSCOPIC MEASUREMENTS

CROSS-REFERENCE TO PRIORITY APPLICATIONS

This application is a continuation of PCT Patent Application Ser. No. PCT/US99/16621, filed Jul. 23, 1999, which in turn claims priority from the following U.S. provisional patent applications: Ser. No. 60/094,275, filed Jul. 27, 1998; Ser. No. 60/117,278, filed Jan. 26, 1999; and Ser. No. 60/136,566, filed May 28, 1999. These PCT and provisional patent applications are each incorporated herein by reference.

CROSS-REFERENCES TO RELATED MATERIALS

This application incorporates by reference the following U.S. patent applications: Ser. No. 09/156,318, filed Sep. 18, 1998; and Ser. No. 09/349,733, filed Jul. 8, 1999.

This application also incorporates by reference the following PCT patent applications: Ser. No. PCT/US98/23095, filed Oct. 30, 1998; Ser. No. PCT/US99/01656, filed Jan. 25, 1999; Ser. No. PCT/US99/03678, filed Feb. 19, 1999; Ser. No. PCT/US99/08410, filed Apr. 16, 1999; Ser. No. PCT/US99/16057, filed Jul. 15, 1999; and Ser. No. PCT/US99/16453, filed Jul. 21, 1999.

This application also incorporates by reference the following U.S. provisional patent applications: Ser. No. 60/094,275, filed Jul. 27, 1998; Ser. No. 60/094,276, filed Jul. 27, 1998; Ser. No. 60/094,306, filed Jul. 27, 1998; Ser. No. 60/1,00,817, filed Sep. 18, 1998; Ser. No. 60/100,951, filed Sep. 18, 1998; Ser. No. 60/104,964, filed Oct. 20, 1998; Ser. No. 60/114,209, filed Dec. 29, 1998; Ser. No. 60/116,113, filed Jan. 15, 1999; Ser. No. 60/117,278, filed Jan. 26, 1999; Ser. No. 60/119,884, filed Feb. 12, 1999; Ser. No. 60/121,229, filed Feb. 23, 1999; Ser. No. 60/124,686, filed Mar. 16, 1999; Ser. No. 60/125,346, filed Mar. 19, 1999; Ser. No. 60/126,661, filed Mar. 29, 1999; Ser. No. 60/130,149, filed Apr. 20, 1999; Ser. No. 60/132,262, filed May 3, 1999; Ser. No. 60/132,263, filed May 3, 1999; Ser. No. 60/135,284, filed May 21, 1999; Ser. No. 60/136,566, filed May 28, 1999; Ser. No. 60/138,311, filed Jun. 9, 1999; Ser. No. 60/138,438, filed Jun. 10, 1999; Ser. No. 60/138,737, filed June 11, 1999; Ser. No. 60/138,893, filed Jun. 11, 1999; and Ser. No. 60/142,721, filed Jul. 7, 1999.

This application also incorporates by reference the following publications: Max Born and Emil Wolf, *Principles of Optics* (6$^{th}$ ed. 1980); Richard P. Haugland, *Handbook of Fluorescent Probes and Research Chemicals* (6$^{th}$ ed. 1996); and Joseph R. Lakowicz, *Principles of Fluorescence Spectroscopy* (1983).

FIELD OF THE INVENTION

The invention relates to spectroscopic assays. More particularly, the invention relates to apparatus and methods for conducting spectroscopic measurements, including absorbance, scattering, reflectance, and luminescence.

BACKGROUND OVERVIEW OF SPECTROSCOPIC ASSAYS

Generally speaking, spectroscopy involves the study of matter using electromagnetic radiation. Spectroscopic measurements can be separated into three broad categories: absorbance, scattering/reflectance, and emission. Absorbance assays involve relating the amount of incident light that is absorbed by a sample to the type and number of molecules in the sample. Absorbance assays are a powerful method for determining the presence and concentration of an analyte in a sample. Most commonly, absorbance is measured indirectly by studying the portion of incident light that emerges from the sample. Scattering assays are similar to absorbance in that the measurement is based on the amount of incident light which emerges or is transmitted from the sample. However, in the case of scattering, the signal increases with the number of interactions, whereas, in the case of absorbance, the signal is inversely proportional to the interactions. Emission assays look at electromagnetic emissions from a sample other than the incident light. In each case, the measurements may be broad spectrum or frequency specific depending on the particular assay.

1. Absorbance Assays

FIG. 1 shows a schematic view of a typical absorbance experiment. Generally, absorbance measurements are made by directing incident light from a light source through a sample and through two walls of a sample container, and measuring the transmitted light using a detector. Unfortunately, this approach has a number of shortcomings. In particular, the sample container may absorb part or all of the incident and transmitted light, decreasing or eliminating the sample signal and increasing the background signal. Moreover, correcting for absorbance by the sample container requires the performance of two experiments, one involving the sample and sample container, and the other involving only the sample container.

The amount of light absorbed by a sample in an absorbance experiment generally may be described by the Beer-Lambert law:

$$\text{Absorbance} = -\log\left(\frac{I(\lambda)}{I_0(\lambda)}\right) = \varepsilon(\lambda)cl \quad (1)$$

The Beer-Lambert law states that when light of wavelength $\lambda$ passes through an absorbing sample, its intensity, I, decreases exponentially. Here, $I_0(\lambda)$ is the intensity of the incident light at wavelength $\lambda$, $I(\lambda)$ is the intensity of the transmitted light, $\varepsilon(\lambda)$ is the decadic molar extinction coefficient, c is the concentration of absorbing molecules, and l is the path length. The quantity $-\log(I/I_0)$ is termed the absorbance and is the logarithm of the reciprocal of the fraction of transmitted light.

Generally, absorbance measurements are most accurate when the absorbance is in the range 0.1–2.0, corresponding to absorption of about 20–99% of the incident light. Yet, in many biological and pharmaceutical applications, such "high" absorbances may be difficult to obtain, because the absorbing molecules may be expensive and/or available in small quantities. Moreover, in many biological and pharmaceutical applications, small samples are desirable, because experimental procedures may involve studying hundreds of thousands of samples, such that small samples decrease reagent costs and the overall space required.

As seen from Equation 1, absorbance may be increased by increasing the concentration of absorbing molecules. Unfortunately, this approach has a number of shortcomings. In particular, because concentration is the number of molecules per unit volume, increasing the concentration involves increasing the number of molecules and/or decreasing the volume. Yet, increasing the number of molecules is undesirable if the molecules are expensive and/or rare. Similarly, decreasing the volume is undesirable because it may decrease the path length and so decrease absorbance.

Also as seen from Equation 1, absorbance may be increased by increasing the path length. Unfortunately, this approach also has a number of shortcomings. In particular, increasing the path length may involve increasing the volume of sample, and hence increasing the number of molecules and the overall space required. Alternatively, increasing the path length may involve decreasing the cross section of the sample, decreasing signal.

2. Scattering Assays

Scattering assays can be used to detect the motion, size, concentration, aggregation state, and other properties of molecules in a sample. For example, by looking at the spectral spread of scattered light, it is possible to determine the average velocity of scattering particles in a sample. By observing the intensity of scattered light, the concentration of scattering objects can be measured. By observing the angular distribution of scattered light, various physical characteristics of scattering molecules can be deduced.

3. Luminescence Assays

Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Luminescence assays are assays that use luminescence emissions from luminescent analytes to study the properties and environment of the analyte, as well as binding reactions and enzymatic activities involving the analyte, among others. In this sense, the analyte may act as a reporter to provide information about another material or target substance that may be the focus of the assay. Luminescence assays may use various aspects of the luminescence, including its intensity, polarization, and lifetime, among others. Luminescence assays also may use time-independent (steady-state) and/or time-dependent (time-resolved) properties of the luminescence. Steady-state assays generally are less complicated than time-resolved assays, but generally yield less information.

A. Intensity Assays

Luminescence intensity assays involve monitoring the intensity (or amount) of light emitted from a composition. The intensity of emitted light will depend on the extinction coefficient, quantum yield, and number of the luminescent analytes in the composition, among others. These quantities, in turn, will depend on the environment of the analyte, among others, including the proximity and efficacy of quenchers and energy transfer partners. Thus, luminescence intensity assays may be used to study binding reactions, among other applications.

B. Polarization Assays

Luminescence polarization assays involve the absorption and emission of polarized light, and typically are used to study molecular rotation. (Polarization describes the direction of light's electric field, which generally is perpendicular to the direction of light's propagation.)

FIG. 2 is a schematic view showing how luminescence polarization is affected by molecular rotation. In a luminescence polarization assay, specific molecules 30 within a composition 32 are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent to which the total emitted light is polarized depends on the extent of molecular reorientation during the time interval between luminescence excitation and emission, which is termed the luminescence lifetime, $\tau$. The extent of molecular reorientation in turn depends on the luminescence lifetime and the size, shape, and environment of the reorienting molecule. Thus, luminescence polarization assays may be used to quantify binding reactions and enzymatic activity, among other applications. In particular, molecules rotate via diffusion with a rotational correlation time $\tau_{rot}$ that is proportional to their size. Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_\| - I_\perp}{I_\| + I_\perp} \tag{2}$$

Here, P is the polarization, $I_\|$ is the intensity of luminescence polarized parallel to the polarization of the excitation light, and $I_\perp$ is the intensity of luminescence polarized perpendicular to the polarization of the excitation light. P generally varies from zero to one-half for randomly oriented molecules (and zero to one for aligned molecules). If there is little rotation between excitation and emission, $I_\|$ will be relatively large, $I_\perp$ will be relatively small, and P will be close to one-half (P may be less than one-half even if there is no rotation; for example, P will be less than one if the absorption and emission dipoles are not parallel.) In contrast, if there is significant rotation between absorption and emission, $I_\|$ will be comparable to $I_\perp$, and P will be close to zero. Polarization often is reported in milli-P (mP) units (1000×P), which for randomly oriented molecules will range between 0 and 500, because P will range between zero and one-half.

Polarization also may be described using other equivalent quantities, such as anisotropy. The relationship between anisotropy and intensity is expressed by the following equation:

$$r = \frac{I_\| - I_\perp}{I_\| + 2I_\perp} \tag{3}$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization and rotation is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (4)$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 Dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 Daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 Daltons and 4,000,000 Daltons.

C. Time-Resolved Assays

Time-resolved assays involve measuring the time course of luminescence emission. Time-resolved assays may be conducted in the time domain or in the frequency domain, both of which are functionally equivalent. In a time-domain measurement, the time course of luminescence is monitored directly. Typically, a composition containing a luminescent analyte is illuminated using a narrow pulse of light, and the time dependence of the intensity of the resulting luminescence emission is observed, although other protocols also may be used. For a simple molecule, the luminescence commonly follows a single-exponential decay.

In a frequency-domain measurement, the time course of luminescence is monitored indirectly, in frequency space. Typically, the composition is illuminated using light whose intensity is modulated sinusoidally at a single modulation frequency f, although other protocols (such as transforming time-domain data into the frequency domain) also may be used. The intensity of the resulting luminescence emission is modulated at the same frequency as the excitation light. However, the emission will lag the excitation by a phase angle (phase) $\phi$, and the intensity of the emission will be demodulated relative to the intensity of the excitation by a demodulation factor (modulation) M.

FIG. 3 shows the relationship between emission and excitation in a single-frequency frequency-domain experiment. The phase $\phi$ is the phase difference between the excitation and emission. The modulation M is the ratio of the AC amplitude to the DC amplitude for the emission, relative to the ratio of the AC amplitude to the DC amplitude for the excitation. The phase and modulation are related to the luminescence lifetime $\tau$ by the following equations:

$$\omega\tau = \tan(\phi) \quad (5)$$

$$\omega\tau = \sqrt{\frac{1}{M^2} - 1} \quad (6)$$

Here $\omega$ is the angular modulation frequency, which equals $2\pi$ times the modulation frequency. For maximum sensitivity, the angular modulation frequency should be roughly the inverse of the luminescence lifetime. Lifetimes of interest in high-throughput screening vary from less than 1 nanosecond to greater than 1 milliseconds. Therefore, instruments for high-throughput screening should be able to cover modulation frequencies from less than about 200 Hz to about 200 MHz.

D. Strengths and Weaknesses of Luminescence Assays

Luminescence methods have several significant potential strengths. First, luminescence methods may be very sensitive, because modern detectors, such as photomultiplier tubes (PMTs) and charge-coupled devices (CCDs), can detect very low levels of light. Second, luminescence methods may be very selective, because the luminescence signal may come almost exclusively from the luminophore.

Luminescence assays also have several significant potential weaknesses. First, luminescence from the analyte might be perturbed in some way, distorting results. For example, if a luminescent analyte binds to the walls of a sample holder during a luminescence polarization assay, the analyte will be unable to rotate, spuriously increasing the polarization. Second, luminescence may arise from sources other than the analyte, contaminating the signal. For example, luminescence may arise from the sample holder, including glass coverslips and plastic microplates.

BRIEF DESCRIPTION OF THE DRAWINGS

FIG. 7 is a schematic view of photoluminescence optical components from the apparatus of FIG. 5.

FIG. 8 is a schematic view of chemiluminescence optical components from the apparatus of FIG. 5.

DETAILED DESCRIPTION OF THE INVENTION

The detailed description is divided into five parts: (1) description of a spectroscopic apparatus, (2) luminescence assays, (3) enhancement of signal, (4) absorbance assays, and (5) scattering assays.

1. Description of Apparatus

Figure 1:
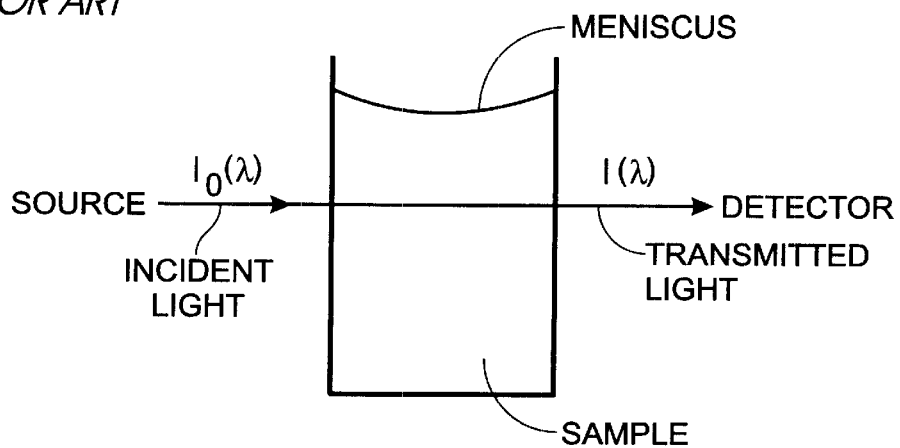
FIG. 1 is a schematic view of a typical absorbance experiment.
Figure 2:
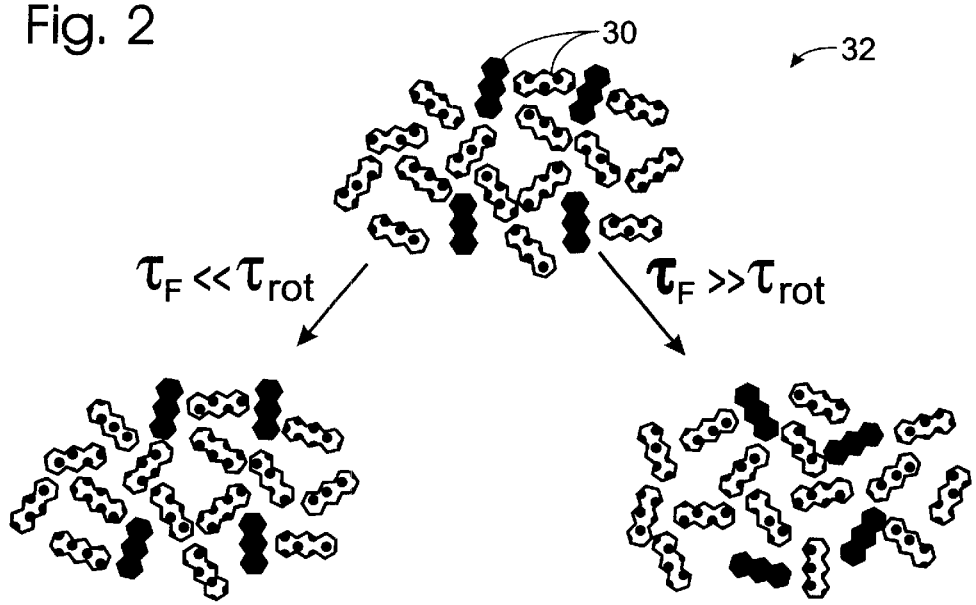
FIG. 2 is a schematic view of luminescently labeled molecules, showing how molecular reorientation affects luminescence polarization.
Figure 3:
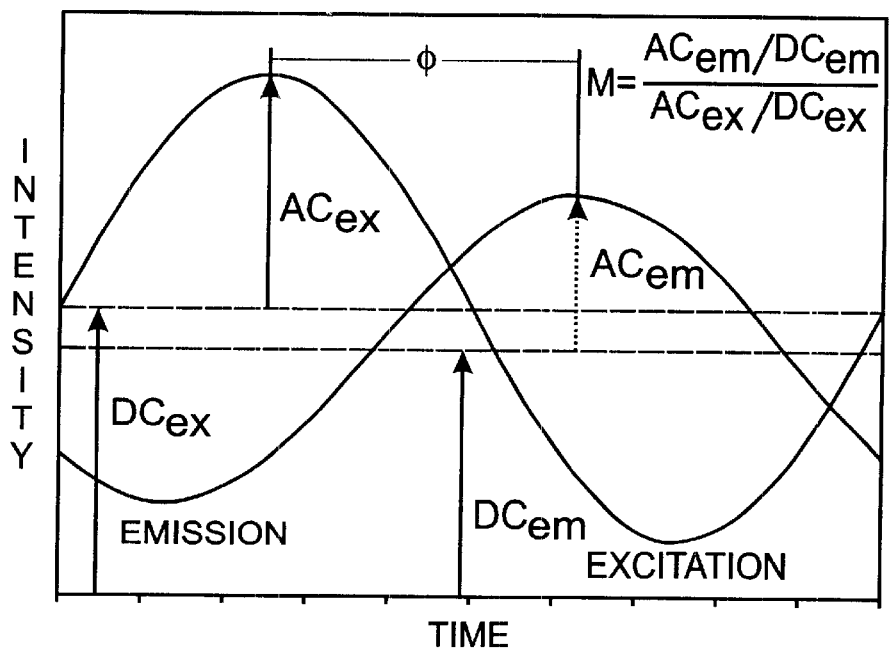
FIG. 3 is a schematic view of a frequency-domain time-resolved measurement, showing the definitions of phase angle (phase) $\phi$ and demodulation factor (modulation) M.
Figure 4:
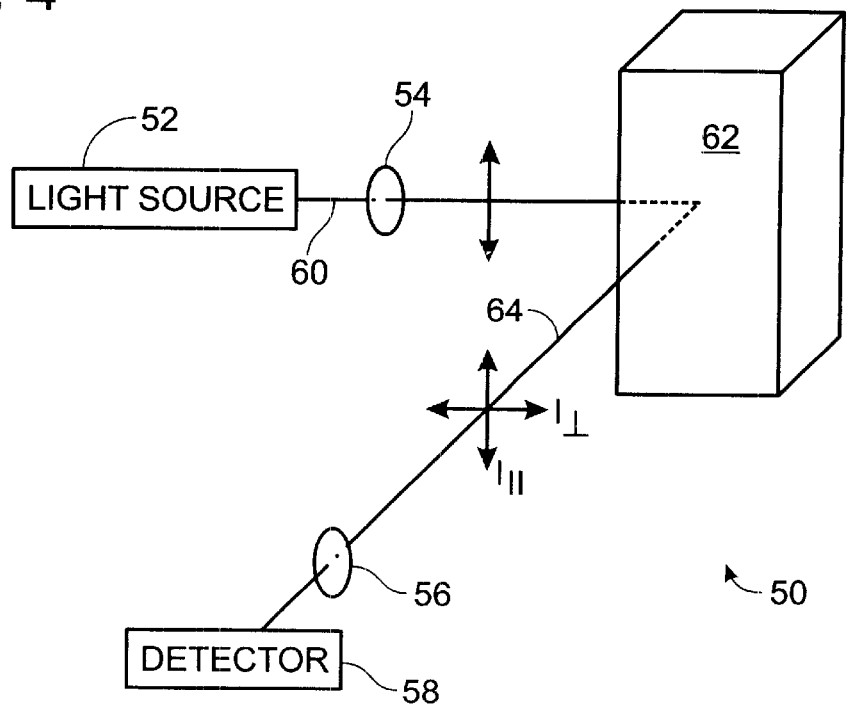
FIG. 4 is a schematic view of an apparatus for detecting light in accordance with the invention.

FIG. 4 shows an apparatus 50 for detecting light (including polarized light) leaving a sample. Apparatus 50 includes a light source 52, an excitation polarizer 54, an emission polarizer 56, and a detector 58. Light 60 produced by light source 52 is directed through excitation polarizer 54, which passes polarized excitation light (indicated by vertical arrow). Polarized excitation light is directed onto a sample 62, which emits light 64 in response. The emitted light may be either some fraction of the incident light or luminescence. Emitted light 64 is directed through emission polarizer 56, which may have components oriented parallel (∥; indicated by vertical arrow) or perpendicular (⊥; indicated by horizontal arrow) to the polarization of excitation light 60. Depending on its orientation, emission polarizer 56 passes parallel ($I_\parallel$) or perpendicular ($I_\perp$) components of emission light 64 for detection by detector 58.

FIGS. 5–8 show an alternative apparatus 90 for detecting light emitted by an analyte in a composition. Apparatus 90 includes (1) a stage for supporting the composition, (2) one or more light sources for delivering light to a composition, (3) one or more detectors for receiving light transmitted from the composition and converting it to a signal, (4) first and second optical relay structures for relaying light between the light source, composition, and detector, and (5) a processor for analyzing the signal from the detector. All or only a subset of these components may be used in any given application.

Apparatus 90 may be used for a variety of assays, including but not limited to the assays described above. Components of the optical system may be chosen to optimize sensitivity and dynamic range for each assay supported by the apparatus. Toward this end, optical components with low intrinsic luminescence are preferred. In addition, some components may be shared by different modes, whereas other components may be unique to a particular mode. For example, in apparatus 90, absorbance, scattering, photoluminescence intensity and steady-state photoluminescence polarization modes share a light source; time-resolved absorbance and luminescence modes use their own light source; and chemiluminescence modes do not use a light source. Similarly, photoluminescence and chemiluminescence modes use different detectors.

The remainder of this section is divided into four subsections: (A) incident light-based optical system, (B) chemiluminescence optical system, (C) housing, and (D) frequency-domain detection system.

A. Incident Light-Based Optical System

FIGS. 8–13 show the incident light-based optical system of apparatus 90. As configured here, apparatus 90 includes a continuous light source 100 and a time-modulated light source 102. Apparatus 90 includes light source slots 103a–d for four light sources, although other numbers of light source slots and light sources also could be provided. Light source slots 103a–d function as housings that may surround at least a portion of each light source, providing some protection from radiation and explosion. The direction of light transmission through the incident light-based optical system is indicated by arrows.

Continuous source 100 provides light for absorbance, scattering, photoluminescence intensity, and steady-state photoluminescence polarization assays. Continuous light source 100 may include arc lamps, incandescent lamps, fluorescent lamps, electroluminescent devices, lasers, laser diodes, and light-emitting diodes (LEDs), among others. A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, averaged over the flash source duty cycle, increasing sensitivity and reducing read times. Apparatus 90 may include a modulator mechanism configured to vary the intensity of light incident on the composition without varying the intensity of light produced by the light source.

Time-modulated source 102 provides light for time-resolved absorbance and/or photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, electronically modulated lasers and LEDs, and continuous lamps and other sources whose intensity can be modulated extrinsically using a Pockels cell, Kerr cell, or other mechanism. Such other mechanisms may include an amplitude modulator such as a chopper as described in U.S. Provisional Patent Application No. 60/094,276, which is incorporated herein by reference. Extrinsically modulated continuous light sources are especially well suited for frequency-domain measurements.

In apparatus 90, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site or measurement region. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In apparatus 90, spectrum is altered by an excitation interference filter 104, which preferentially transmits light of preselected wavelengths and preferentially absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103*a,b*, but not other light source slots 103*c,d*. Alternatively, the filter wheel may include a blank station that does not affect light passage.

Light next passes through an excitation optical shuttle (or switch) 108, which positions an excitation fiber optic cable 110*a,b* in front of the appropriate light source to deliver light to top or bottom optics heads 112*a,b*, respectively. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In apparatus 90, polarization is altered by excitation polarizers 114, which are included only with top optics head 112*a* for top reading; however, such polarizers also can be included with bottom optics head 112*b* for bottom reading. Excitation polarization filters 114 may include an s-polarizer S that passes only s-polarized light, a p-polarizer P that passes only p-polarized light, and a blank O that passes substantially all light. Excitation polarizers 114 also may include a standard or ferro-electric liquid crystal display (LCD) polarization switching system. Such a system is faster and more economical than a mechanical switcher. Excitation polarizers 114 also may include a continuous mode LCD polarization rotator with synchronous detection to increase the signal-to-noise ratio in polarization assays. Excitation polarizers 114 may be incorporated as an inherent component in some light sources, such as certain lasers, that intrinsically produce polarized light.

Light at one or both optics heads also may pass through an excitation "confocal optics element," which generally comprises any mechanism for focusing light into a "sensed volume." In apparatus 90, the confocal optics element includes a set of lenses 117*a–c* and an excitation aperture 116 placed in an image plane conjugate to the sensed volume, as shown in FIG. 7. Aperture 116 may be implemented directly, as an aperture, or indirectly, as the end of a fiber optic cable. Preferred apertures have diameters of 1 mm and 1.5 mm. Lenses 117*a,b* project an image of aperture 116 onto the sample, so that only a preselected or sensed volume of the sample is illuminated. The area of illumination will have a diameter corresponding to the diameter of the excitation aperture.

Light traveling through the optics heads is reflected and transmitted through a beamsplitter 118, which delivers reflected light to a composition 120 and transmitted light to a light monitor 122. Reflected and transmitted light both pass through lens 117*b*, which is operatively positioned between beamsplitter 118 and composition 120.

Beamsplitter 118 is used to direct excitation or incident light toward the sample and light monitor, and to direct light leaving the sample toward the detector. The beamsplitter is changeable, so that it may be optimized for different assay modes or compositions. If a large number or variety of photoactive molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable light leaving the sample to the detector. If one or a few related photoactive molecules are to be studied, the beamsplitter needs only to be able to accommodate light at a limited number of wavelengths; in this case, a "dichroic" or "multichroic" beamsplitter is optimal. Such a beamsplitter can be designed with cutoff wavelengths for the appropriate sets of molecules and will reflect most or substantially all of the excitation and background light, while transmitting most or substantially all of the emission light in the case of luminescence. This is possible because the beamsplitter may have a reflectivity and transmissivity that varies with wavelength.

Light monitor 122 is used to correct for fluctuations in the intensity of light provided by the light sources. Such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The composition (or sample) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof Analysis of the composition may involve measuring the presence, concentration, or physical properties (including interactions) of a photoactive analyte in such a composition. Composition may refer to the contents of a single microplate well, or several microplate wells, depending on the assay. In some embodiments, such as a portable apparatus, the stage may be intrinsic to the instrument.

The sample holder can include microplates, biochips, or any array of samples in a known format. In apparatus 90, the preferred sample holder is a microplate 124, which includes a plurality of microplate wells 126 for holding compositions. Microplates are typically substantially rectangular holders that include a plurality of sample wells for holding a corresponding plurality of samples. These sample wells are normally cylindrical in shape although rectangular or other shaped wells are sometimes used. The sample wells are typically disposed in regular arrays. The "standard" microplate includes 96 cylindrical sample wells disposed in a 8×12 rectangular array on 9 millimeter centers.

The sensed volume typically has an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume, as described in PCT Patent Application Ser. No. PCT/US99/08410, which is incorporated herein by reference.

Figure 5:
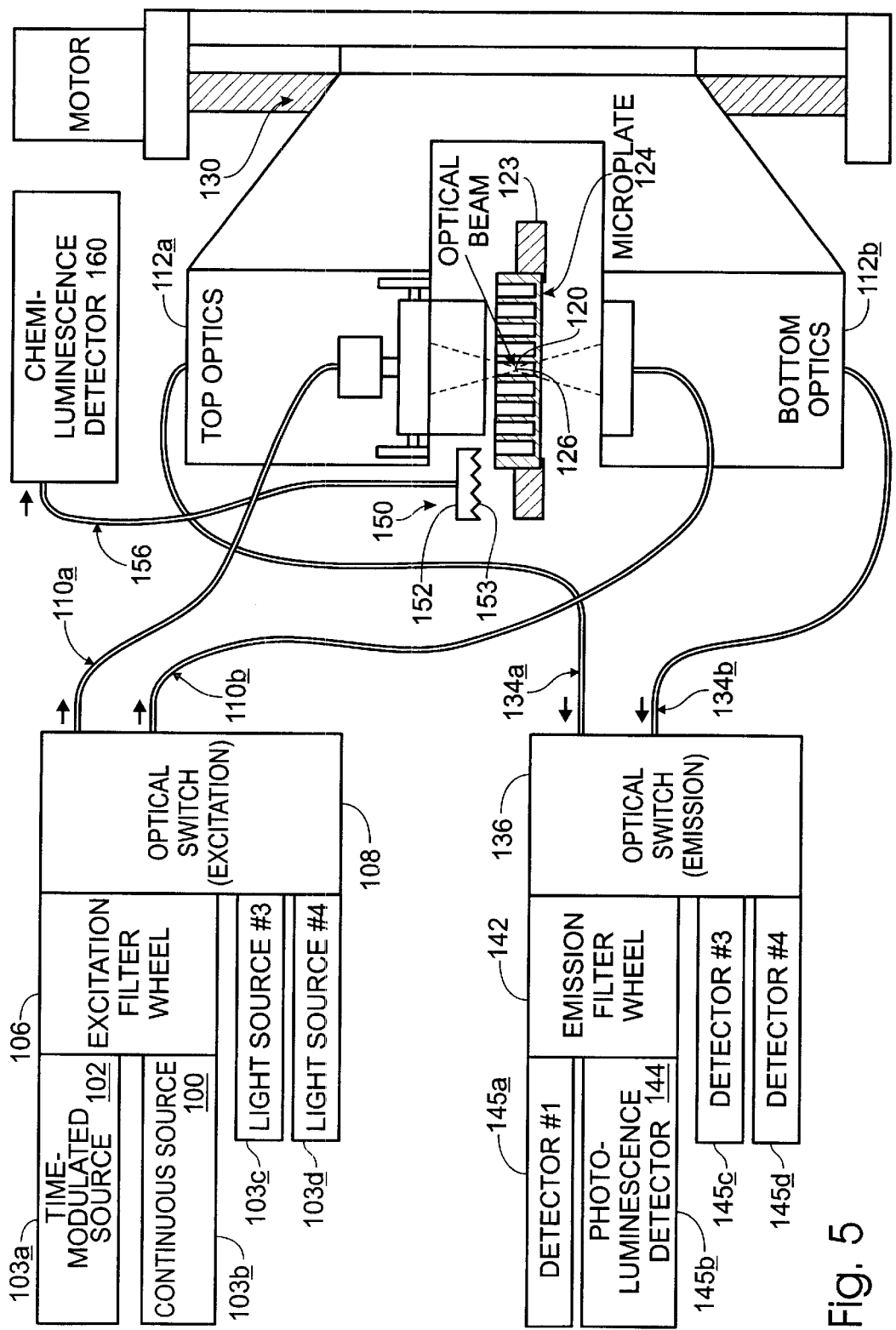
FIG. 5 is a schematic view of an alternative apparatus for detecting light in accordance with the invention.
Figure 6:
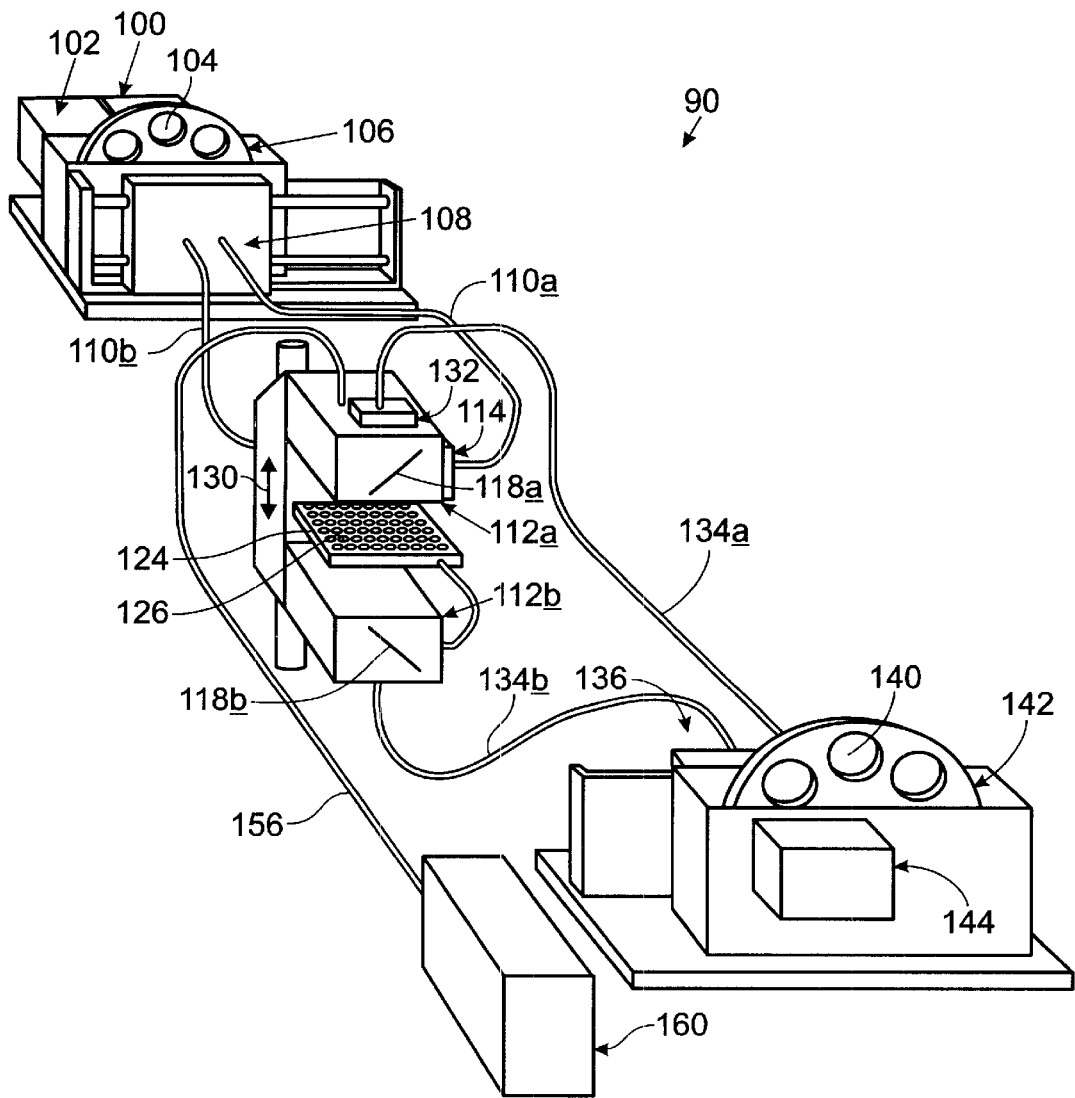
FIG. 6 is a partially schematic perspective view of the apparatus of FIG. 5.

The position of the sensed volume can be moved precisely within the composition to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In apparatus 90, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 5 and 6. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection (1) and (4) is referred to as "epi" and is preferred for photoluminescence and scattering assays. Opposite-side illumination and detection (2) and (3) is referred to as "trans" and has been used in the past for absorbance assays. In apparatus 90, epi modes are supported, so the excitation and emission light travel the same path in the optics head, albeit in opposite or anti-parallel directions. However, trans modes also can be used with additional sensors, as described below. In apparatus 90, top and bottom optics heads move together and share a common focal plane. However, in other embodiments, top and bottom optics heads may move independently, so that each can focus independently on the same or different sample planes.

Generally, top optics can be used with any sample holder having an open top, whereas bottom optics can be used only with sample holders having optically transparent bottoms, such as glass or thin plastic bottoms. Clear bottom sample holders are particularly suited for measurements involving analytes that accumulate on the bottom of the holder.

Light is transmitted by the composition in multiple directions. A portion of the transmitted light will follow an emission pathway to a detector. Transmitted light passes through lens 117c and may pass through an emission aperture 131 and/or an emission polarizer 132. In apparatus 90, the emission aperture is placed in an image plane conjugate to the sensed volume and transmits light substantially exclusively from this sensed volume. In apparatus 90, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In apparatus 90, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In apparatus 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters may be changed manually, or they may be changed automatically, for example, by using a filter wheel. Intensity filters also may divert a portion of the light away from the sample without absorption. Examples include beam splitters, which transmit some light along one path and reflect other light along another path, and Pockels cells, which deflect light along different paths through diffraction. Examples also include hot mirrors or windows that transmit light of some wavelengths and absorb light of other wavelengths.

Light next may pass through an emission interference filter 140, which may be housed in an emission filter wheel 142. In apparatus 90, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance, scattering and photoluminescence assays. In apparatus 90, there is one detector 144, which detects light from all modes. A preferred detector is a photomultiplier tube (PMT). Apparatus 90 includes detector slots 145a–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, an&or (3) imaging modes, among others, as described in PCT Patent Application Ser. No. PCT/US99/03678.

B. Chemiluminescence Optical System

FIGS. 5, 6, and 8 show the chemiluminescence optical system of apparatus 50. Because chemiluminescence follows a chemical event rather than the absorption of light, the chemiluminescence optical system does not require a light source or other excitation optical components. Instead, the chemiluminescence optical system requires only selected emission optical components. In apparatus 50, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the incident light-based optical system. The chemiluminescence optical system also can be used for other assay modes that do not require illumination, such as electrochemiluminescence.

The chemiluminescence optical path begins with a chemiluminescent composition 120 held in a sample holder 126. The composition and sample holder are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample holder. A portion of the light transmitted through the top of the well is collected using a chemiluminescence head 150, as shown in FIG. 5, and will follow a chemiluminescence optical pathway to a detector. The direction of light transmission through the chemiluminescence optical system is indicated by arrows.

The chemiluminescence head includes a nonconfocal mechanism for transmitting light from a sensed volume within the composition. Detecting from a sensed volume reduces contributions to the chemiluminescence signal resulting from "cross talk," which is pickup from neighboring wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156, which may be replaced by any suitable mechanism for directing light from the composition toward the detector. Fiber optic cable 156 is analogous to excitation and emission fiber optic cables 110a,b and 134a,b in the photoluminescence optical system. Fiber optic cable 156 may include a transparent, open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In apparatus 50, intensity is altered by chemiluminescence neutral density filters 158. Light also may pass through other filters, if desired.

Light last passes to a detector, which converts light into signals that may be processed by the apparatus. In apparatus 50, there is one chemiluminescence detector 160. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

C. Housing

Figure 9:
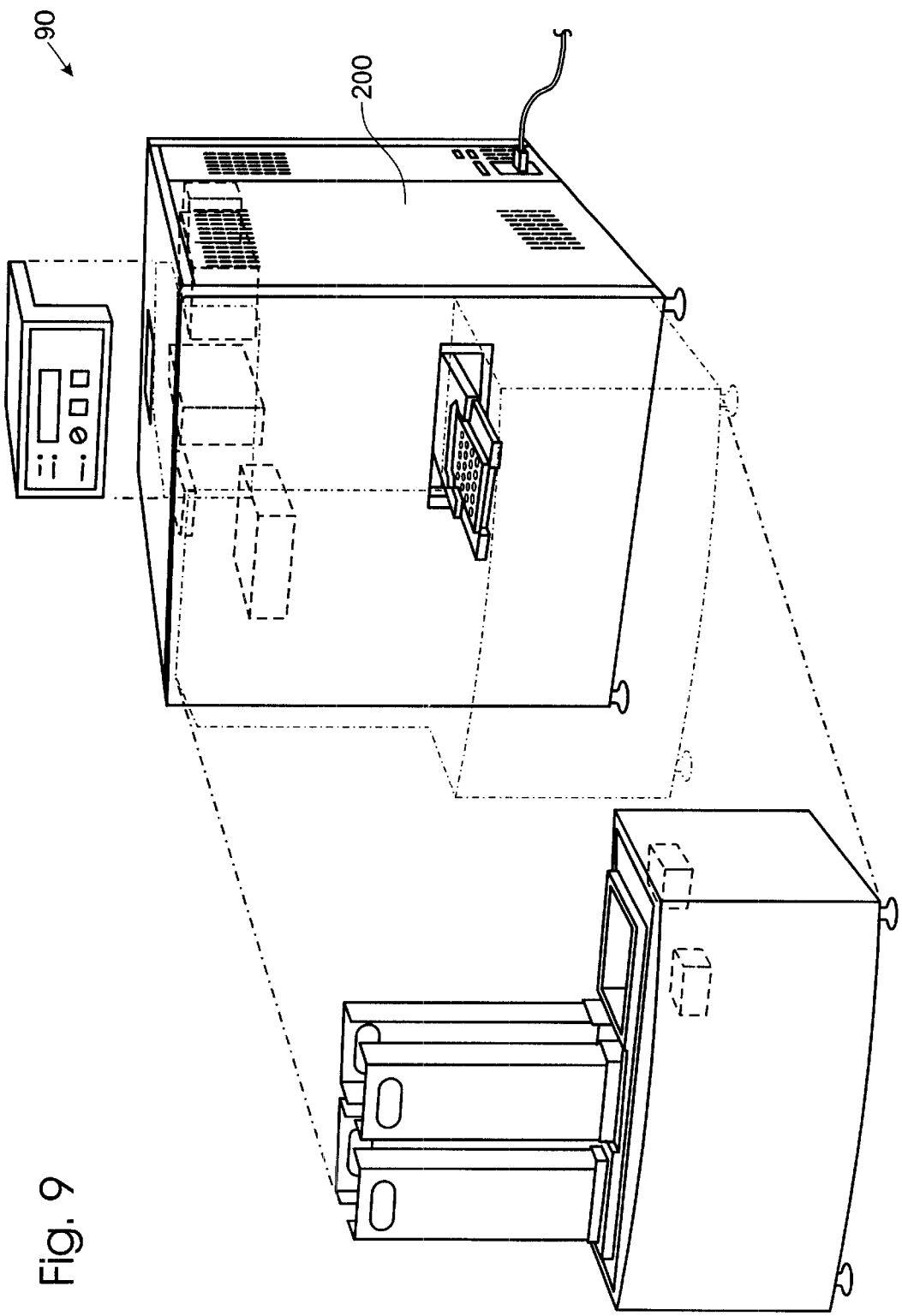
FIG. 9 is a partially exploded perspective view of a housing for the apparatus of FIG. 5.

FIG. 9 shows a housing 200 and other accessories for the apparatus of FIGS. 5–8. Housing 200 substantially encloses the apparatus, forming (together with light source slots 103a–d) two protective layers around the continuous high color temperature xenon arc lamp. Housing 200 permits automated sample loading and switching among light sources and detectors, further protecting the operator from the xenon arc lamp and other components of the system. Additional details of an apparatus suitable for implementing features of the invention are shown in U.S. patent application Ser. No. 09/160,533, which is incorporated herein by reference.

D. Frequency-domain Detection System

Figure 10:
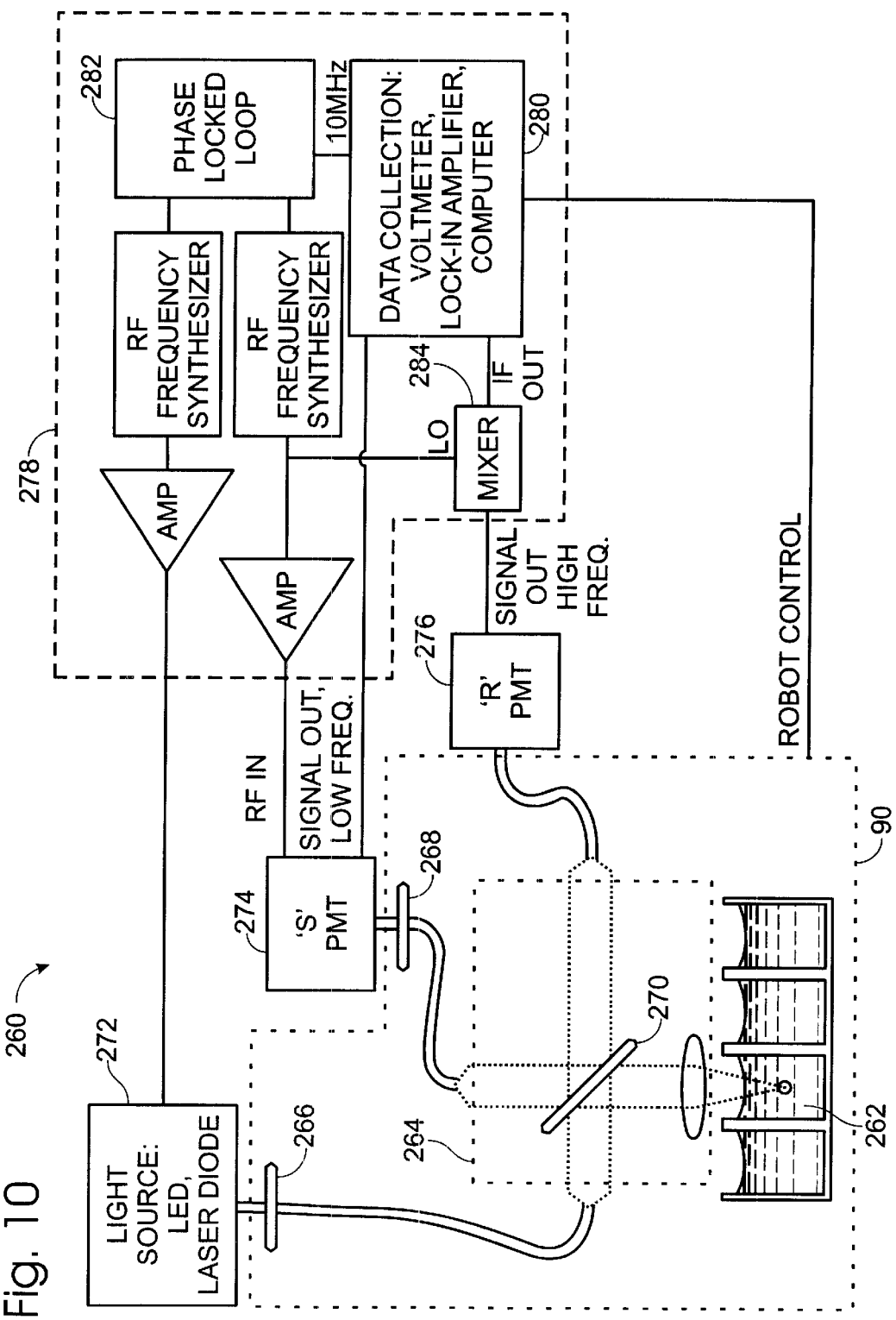
FIG. 10 is a schematic view of an alternative apparatus for detecting light in accordance with the invention.

FIG. 10 shows an apparatus 260 for detecting light emitted by an analyte in a composition 262, where the detection and/or processing may be performed in the frequency-domain. Apparatus 260 includes substantial portions of apparatus 90, including its fiber-optic-coupled optics head 264, excitation 266 and emission 268 filters, dichroic beam splitter 270, and mechanisms for sample positioning and focus control. However, apparatus 260 also may include alternative light sources 272, sample ('S') detectors 274, reference ('R') detectors 276, and detection electronics 278. In FIG. 10, alternative components 272–278 are shown outside apparatus 90, but they readily may be included inside housing 250 of apparatus 90, if desired.

Apparatus 260 may provide incident light in various ways, as described above. For example, analytes absorbing blue light may be excited using a NICHIA-brand bright-blue LED (Model Number NSPB500; Mountville, Pa.). This LED produces broad-spectrum excitation light, so excitation filter 266 may be selected to block the red edge of the spectrum. If analytes are excited using a laser diode, an excitation filter is not necessary.

Apparatus 260 may detect emitted light and convert it to a signal in various ways. This demodulation/deconvolution may be internal to the photodectector, or it may be performed with external electronics or software. For example, emitted light can be detected using sample detector 274, which may be an ISS-brand gain-modulated PMT (Champaign, Ill.). High-frequency emitted light can be frequency down-converted to a low-frequency signal using a technique called heterodyning. The phase and modulation of the low-frequency signal can be determined using a lock-in amplifier 280, such as a STANFORD RESEARCH SYSTEMS brand lock-in amplifier (Model Number SR830; Sunnyvale, Calif.). Lock-in amplifier 280 is phase locked using a phase-locked loop 282 to the modulation frequency of light source 272. To correct for drift in the light source, the output of light source 272 may be monitored using reference detector 276, which may be a HAMAMATSU-brand PMT (Model Number H6780; Bridgewater, N.J.). If reference detector 276 can respond to high-frequency signals, the heterodyning step can be performed using an external mixer 284. The phase and modulation of reference detector 276 also may be captured by lock-in amplifier 280 and used to normalize the signal from sample detector 274.

A computer or processor controls the apparatus, including the external components. The computer also directs sample handling and data collection. Generally, phase and modulation data are collected at one or more frequencies appropriate for the lifetime of the analyte. In some cases, phase and modulation may be measured at one or a few frequencies and processed by the computer or processor to help reduce detected background.

The invention also may employ other apparatus or optical devices having yet other combinations of components. Such apparatus and devices may have a high color temperature light source and/or be capable of detecting light substantially exclusively from a sensed volume.

2. Luminescence Assays

Apparatus 50, 90, and 260 may be used to conduct a variety of steady-state and time-resolved luminescence assays. Steady-state assays measure luminescence under constant illumination, using the continuous light source. Time-resolved polarization assays measure luminescence as a function of time, using either the continuous light source, with its intensity appropriately modulated, or the time-varying light source.

A. Intensity Assays

Intensity assays may be conducted by monitoring the intensity of the luminescence emitted by the composition.

B. Polarization Assays

Polarization assays may be conducted as follows. Excitation light from the continuous light source is directed through an excitation filter, low-luminescence fiber optic cable, and excitation polarization filter. Excitation light then is directed to a beamsplitter, which reflects most of the light onto a composition and transmits a little of the light into a light monitor. Emitted light from the composition is directed back through the beamsplitter and then is directed through another low-luminescence fiber optic cable, an emission filter, and a polarization filter (in either the S or P orientation) before detection by a photomultiplier tube or. other detector. Two measurements are performed for each composition, one with excitation and emission polarizers aligned and one with excitation and emission polarizers crossed. Either polarizer may be static or dynamic, and either polarizer may be set in the S or P orientation, although typically the excitation polarizer is set in the S orientation.

Steady-state polarization assays also may be conducted by constantly polarizing and transmitting high color temperature light to an examination site as successive samples are automatically, serially aligned in an optical path intersecting the examination site, and detecting polarized light emitted from each sample.

C. Miscellaneous Assays

Additional detection methods are presented in PCT Patent Application Ser. Nos. PCT/US99/01656 and PCT/US99/03678, which are incorporated herein by reference, as well as other patent applications and books listed above under Cross-References.

Additional luminescence assays, including fluorescence resonance energy transfer (FRET), fluorescence lifetime (FLT), total internal reflection fluorescence (TIR), fluorescence correlation spectroscopy (FCS), and fluorescence recovery after photobleaching (FRAP), as well as their phosphorescence analogs, may be conducted using procedures outlined in the patent applications and books cross-referenced above and/or generally known to persons of ordinary skill in the art.

3. Enhancement of Signal

Achieving good signal-to-noise and signal-to-background ratios from dilute samples is critical in absorbance, scattering, luminescence polarization and other assays supported by the apparatus. For example, in a binding assay, it often is desirable to be able to probe binding involving molecules with dissociation constants in the sub-nanomolar range. This is facilitated by being able to achieve acceptable signal-to-noise and signal-to-background ratios from compositions with luminophore concentrations in the sub-nanomolar range. The methods of signal-to-noise and signal-to-background enhancement discussed below permit the apparatus to achieve the required sensitivity with such dilute samples, thereby minimizing reagent cost, which otherwise can be considerable.

Sensitivity also is enhanced by reducing the contribution of noise to the measurements. In luminescence polarization assays, various factors contribute to noise, including (1) background noise and (2) intensity noise. Background noise refers to contributions to the signal from luminescent species other than the luminescent species of interest, including luminescent species in the apparatus and sample holder. Intensity noise refers to fluctuations in light intensity, including those arising from photon noise.

Background noise may be reduced by reducing autoluminescence from the apparatus and sample holder. For example, the apparatus may use low luminescence components, such as fused silica fiber optic cables. Similarly, the sample holder may be constructed using low luminescence materials, such as black polystyrene and/or carbon black. Suitable microplate compositions are described in PCT Patent Application Serial No. PCT/US99/08410, which is incorporated herein by reference.

Background noise also may be reduced by reducing detection of luminescence from components of the sample that are bound to the sample holder and immobilized, which otherwise would lead to spuriously high luminescence polarization. For example, the walls of the sample holder may be constructed or treated to reduce binding. Alternatively, in an apparatus capable of detecting light transmitted substantially exclusively from a sensed volume, the sensed volume may be positioned near the center of the composition, away from the walls of the sample holder.

Intensity noise may be reduced by correcting for fluctuations in light source intensity, among others. Light source fluctuations arise due to fluctuations in power from the power supply and drift in the position of the arc in arc lamps, among others. Light source fluctuations will lead to luminescence fluctuations, because the amount of emitted light in luminescence or absorbance is proportional to the amount of excitation light. Luminescence fluctuations are especially important in polarization assays, because such assays involve comparing the magnitude of successively measured signals. Light source fluctuations may be reduced by choosing a stable light source and by resealing the emitted light signal using information obtained from a light source monitor, as described above.

Intensity noise also may be reduced by increasing the number of photons (amount of light) detected, which reduces photon noise. Photon (or shot) noise arises due to the statistical nature of light and may be described by the same statistical law used to describe radiation decay. In particular, if N photons are detected during a given time interval, the standard deviation associated with that number due to photon noise will be $\sqrt{N}$. The relative significance of photon noise decreases as the number of detected photons increases, because the ratio of the standard deviation in the signal to the signal goes as $\sqrt{N}/N=1/\sqrt{N}$. Although there may be many sources of intensity noise, the limit set by photon noise can never be overcome; however, the significance of photon noise can be reduced by increasing the number of photons collected by the detector. The number of photons collected may be increased by increasing the intensity of the light source, the efficiency of the detector, and/or the throughput of components of the optical relay structure, such as the beamsplitter, among others.

Photon noise creates noise in polarization assays. To a very good approximation, the noise in the polarization is proportional to the noise in the intensities from which the polarization is calculated and corresponds to seven mP standard deviation in polarization for every one percent standard deviation in intensity. This relationship essentially is independent of the degree of polarization. Because of photon noise, the requirement for rapid high-throughput screening measurements in the optically restrictive microplate format puts a premium on simply collecting enough light. For additional information, see PCT Patent Application Serial No. PCT/US98/23095, which is incorporated herein by reference.

Most well-developed polarization assays have maximum polarization changes of between 100 mP and 200 mP, so acceptable standard deviations in the polarization should be no greater than about 5 mP to 10 mP. This requires detection of at least 10,000 photons per intensity measurement to reduce intensity noise to about 1%. The inefficiency of polarization optical systems increases the problem. The number of photons collected is proportional to both the concentration and the detection time, leading to trade-offs between probe concentration and screening throughput. High concentrations of reagents not only are expensive, but also produce insensitive binding assays if they exceed the dissociation constant of the binding reaction.

The various absorbance and scattering assays described below can also be used in conjunction with luminescence assays to improve accuracy. For example, a sample that has significant absorbance or scattering will have reduced luminescence signal. By monitoring absorbance or scattering, it is possible to correct for changes in luminescence that are a result of absorbance or scattering variations.

4. Absorbance Assays

Figure 11:
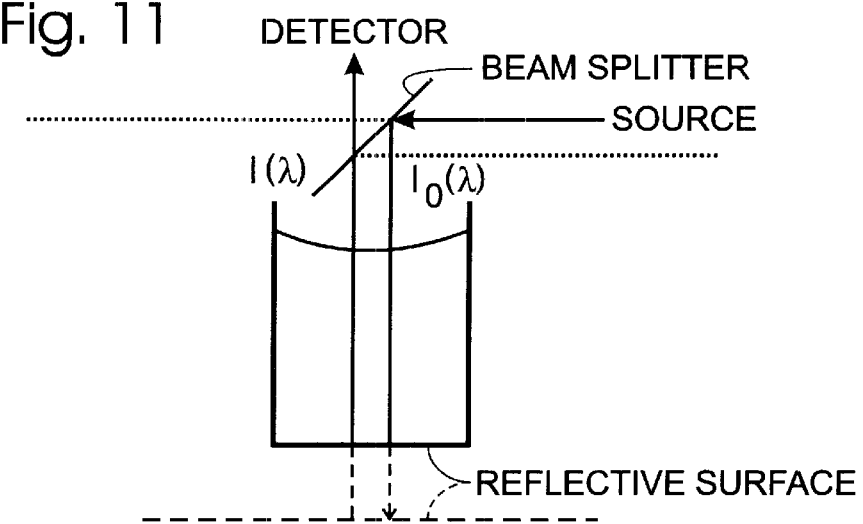
FIG. 11 is a schematic view of an absorbance experiment conducted in accordance with the invention.

FIG. 11 shows a schematic view of an absorbance assay performed in accordance with the invention. Incident light from a light source is reflected onto the sample by a beam splitter. The light passes a first time through the sample, bounces off a reflective surface at the far side of the sample, and passes back a second time through the sample. Transmitted light emerges from the sample and passes through the beam splitter to a detector. The optical paths between the light source and sample, and the sample and light detector, may lie along different optical axes, or they may lie along the same optical axis, as when a fiber optic bundle having parallel excitation and emission fibers is employed.

In a preferred embodiment, the absorbance assay is performed using a high-throughput analyzer, such as described above and disclosed in the patent applications cross-referenced above. In this embodiment, a 50/50 beam splitter is employed, one of the two spectral filters normally used for luminescence is removed, and the other of the two spectral filters is selected to match an absorbance band of interest of the sample. In addition, the focal plane of the confocal optics is adjusted so that the instrument focuses on the far side of the sample container. It should be noted that than attenuator may be necessary between the sample and the detector to reduce the light level to a range useable by the detector. Because luminescence levels are typically very low compared to incident light levels and reflected light levels, the majority of the light reaching the detector will consist of reflected light that has passed twice through the sample in the described arrangement. Where reflected light levels are lower, it is also possible to filter out luminescence light or other light sources so that primarily reflected light reaches the detector. A reference sample well containing a blank, i.e. without the analyte of interest, may be used to correct for absorbance by the solution, optics, or other non-sample components of the assay. In a preliminary experiment in a 96-well microplate, absorbance over a range of 1.2 ODs was measured with about 0.1 OD resolution and acceptable linearity.

The reflective surface may include the sample wall or an additional surface. For example, the reflective surface may include a partially reflective sample wall, such as the bottom of a clear microplate, the interior surface of a white microplate, or a totally reflective sample wall, such as sample wall with a silvered surface. Alternatively, the reflective surface may include an additional surface, such as a mirror placed inside or outside the sample container, as shown by the dashed lines in FIG. 11. Reflection from the reflective surface may occur by a variety of mechanisms, including total internal reflection.

Figure 12:
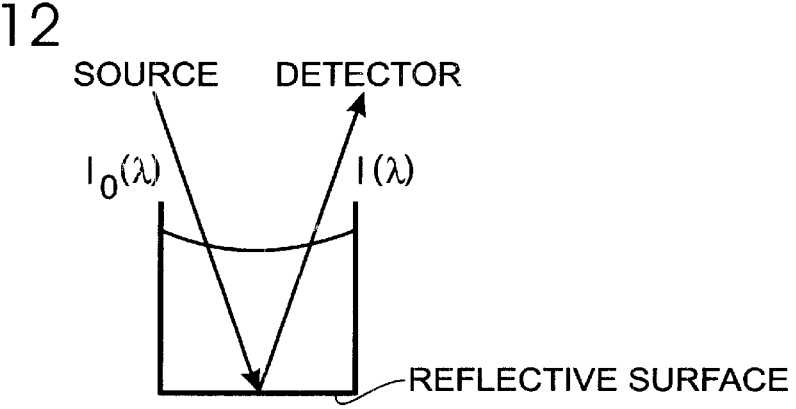
FIG. 12 is a schematic view of an alternative absorbance experiment conducted in accordance with the invention.

FIG. 12 shows a schematic view of an alternative absorbance assay performed in accordance with the invention. Light enters and exits through an open side of the sample container, and may be reflected by the sample wall or by a mirror inside or outside the sample wall. This alternative absorbance assay does not involve a beam splitter, and may not involve passage of light through any wall of the sample container. This alternative absorbance assay does provide an extended path length, which arises because light travels through the sample at an angle, further increasing absorbance. Path length similarly may be extended in other embodiments, including embodiments incorporating beam splitters.

Figure 13:
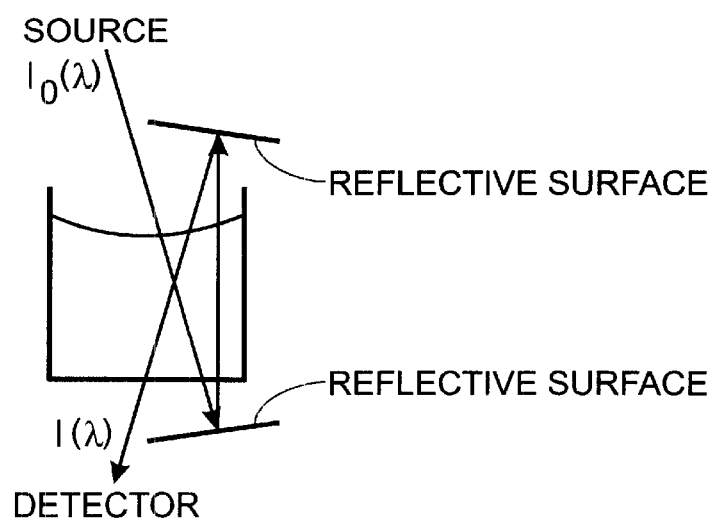
FIG. 13 is a schematic view of another alternative absorbance experiment conducted in accordance with the invention.

FIG. 13 shows that light may be directed through the sample more than twice.

The absorbance assay minimizes the influence of the sample meniscus on assay results. In particular, refractive effects due to the meniscus are minimized because they are reversed on the return trip after the light reflects off the far side of the sample container. Additional corrections for effects such as meniscus variations may be made by referencing a measurement at the wavelength at which absorbance is to be determined by an absorbance-mode measurement in the same sample container at one or more other wavelengths where there is no absorption, essentially a ratiometric strategy.

As mentioned above, absorbance assays also may be used to improve fluorescence and other luminescence assays. For example, absorbance measurements can be paired with luminescence measurements to detect "color quenching" of fluorescence assays. "Color quenching" is a term used to describe the absorbance of excitation or luminescence emission light in samples that happen to have significant extinction coefficients at those wavelengths. The result is a decrease in the measured luminescence intensity, which may significantly interfere with assay interpretation. The result of an absorbance measurement can be used to correct the measured luminescence back to the value that would have been obtained in the absence of absorbance.

A separate, simultaneous or subsequent absorbance measurement made at the excitation and/or emission wavelength can identify the existence of color quenching and may provide a means of correcting the luminescence signal for this interference. If a dichroic beamsplitter is used for the luminescence measurements, the beamsplitter will significantly attenuate the signal used in the absorbance measurement. It is preferable not to have to switch to a wavelength-insensitive (e.g., 50/50) beamsplitter when making the absorbance measurement after the luminescence measurement. The intensity of the reflected light used in the absorbance measurement generally will be much higher than the intensity of luminescence and may be attenuated before reaching the detector; the attenuation caused by the dichroic beam splitter likely can serve this function.

Figure 14:
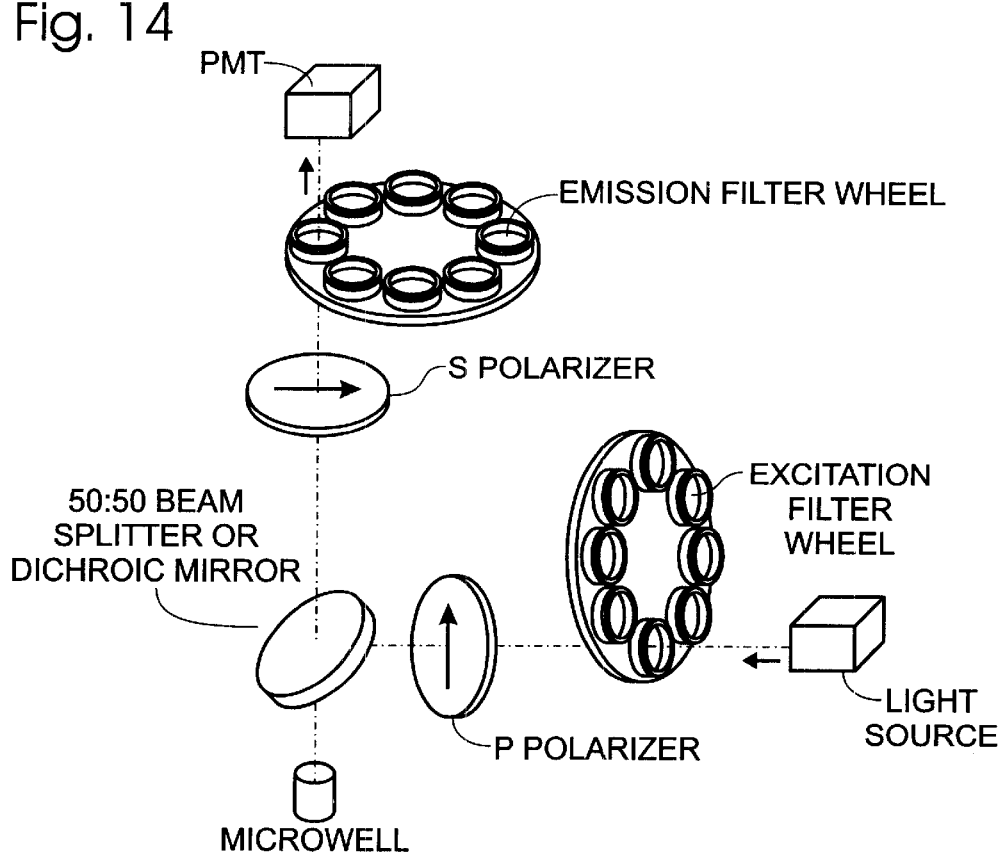
FIG. 14 is a schematic view of an apparatus for conducting an absorbance experiment, in which the apparatus is constructed in accordance with the invention.

FIG. 14 shows an apparatus for conducting an absorbance measurement constructed in accordance with the invention. The apparatus employs the reflective absorbance configured as described above. The apparatus can give a simultaneous indication of reflectance, scattering, and absorbance of a sample in a microplate well or other sample container in a top down (i.e., non-transmissive) configuration. This method can be used with white, black, or clear bottom microplates. The sensitivity of the method can be enhanced with the insertion of crossed polarizers. Reflective absorbance sensitivity is further optimized by selection of the appropriate focal height within the sample well.

The response linearity of this method can be improved by determining the amount of "excess intensity" (which includes background light and reflected light) and subtracting it from the raw intensities prior to calculating the absorbance. Mathematically, the raw intensity $I_{Raw}$ was assumed to include light that passed through the sample $I_{Sample}$ and instrument background $I_{Bkg}$:

$$I_{Raw} = I_{Sample} + I_{Bkg} \tag{7}$$

The raw intensities then were curve-fit to a pseudo-Beer's law model, where $I_{Bkg}$ and K were selected using a nonlinear least-squares fitting method:

$$A = -\log_{10}\left[\frac{I_{Raw} - I_{Bkg}}{I_{RawBuffer} - I_{Bkg}}\right] = K \times C_{Sample} \tag{8}$$

This sample linearization scheme can be used to produce reasonably linear responses over >2 optical density (OD) units in certain cases.

Reflective absorbance is particularly suitable for use with white microplates or any plate with a strong scatterer settled on the bottom, due to the strong scattering effect at the inner surface of the microplate wells. This scattering (and depolarization) effect can be caused by the addition of a high dielectric constant material like titanium dioxide to the plastic from which the microplate is molded. Alternatively, scattering and depolarization can be caused by the presence of an optically active layer of small beads on the bottom of the well that have scattering properties (e.g., scintillation proximity assay (SPA) beads). The excitation light that is back-scattered from the well inner surface emerges from the microplate well highly depolarized. The use of crossed polarizers in the configuration shown in FIG. 14 causes back-reflected polarized light to be strongly attenuated by the second polarizer, enhancing the signal-to-background ratio. Highly polarized input light travels through the sample and is scattered and de-polarized when it hits the bottom surface of the microplate well. Back-scattered depolarized light that passed through the sample (and is absorbed or reflected by it) is preferentially passed through the crossed polarizers, whereas back-reflected polarized light from optical surfaces or the meniscus in the microplate well is highly attenuated because it retains a high polarization. In some applications, it may be possible to eliminate undesired contributions to a signal using two polarizers in alternative orientations, including generally parallel.

If the measurement conditions are optimized, reflective absorbance can be used in high throughput screening to detect and potentially correct for potential interferences from absorbing, scattering, compounds, targets, reagents, contaminants, etc. For example, reflective absorbance could be used to correct for color quenching in scintillation proximity assays or absorbing or luminescing compounds in intensity-based luminescence or chemiluminescence based assays.

Figure 15:
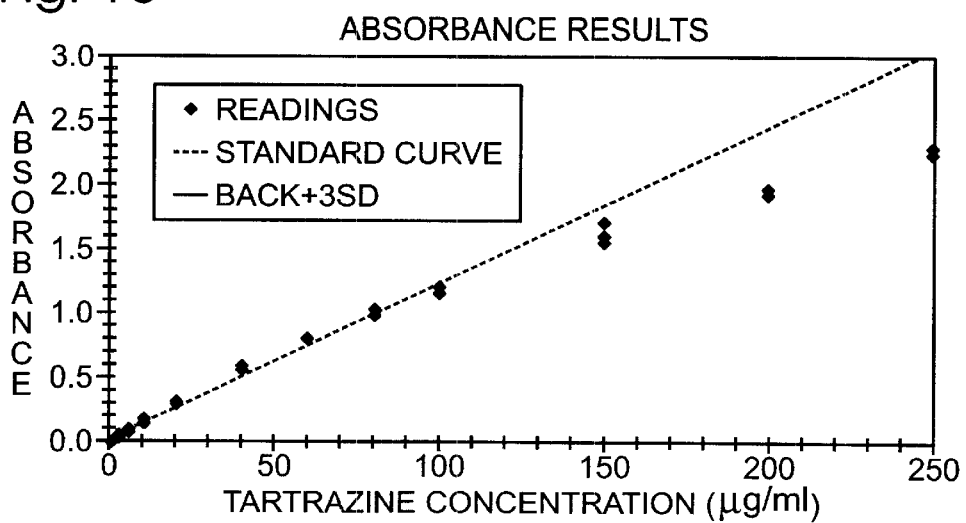
FIG. 15 is a graph of reflective absorbance results obtained in accordance with the invention.
Figure 16:
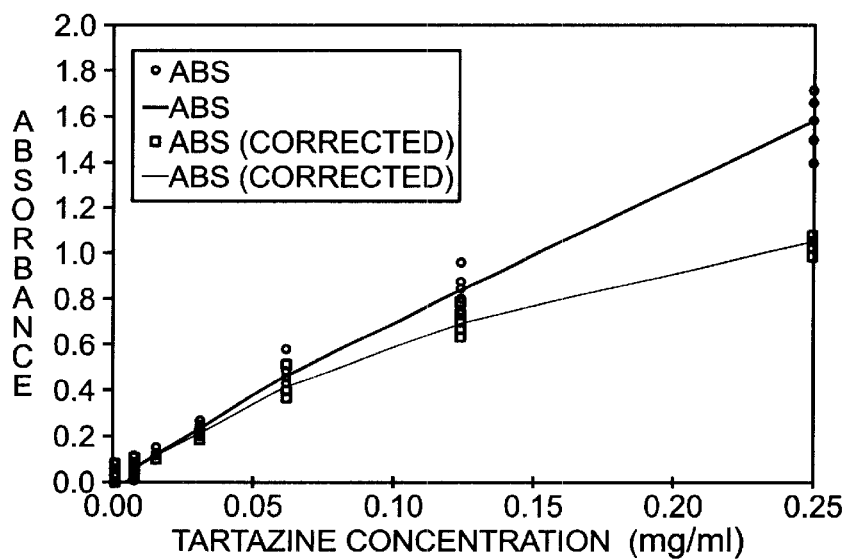
FIG. 16 is a graph of reflective absorbance results obtained in accordance with the invention, showing that the resolution of the assay may be improved using information obtained from a blank.

FIGS. 15 and 16 show experimental results obtained in accordance with the invention. The apparatus employed an ANALYST high-throughput detection platform, which included a confocal optical arrangement and a 50/50 beam splitter. The adjustable z height was set so that the instrument focused on the bottom of the well. Transmission (or absorbance) was measured by bouncing light off the bottom of a clear bottom microplate to get two passes through the liquid. The change in signal between a reference well and the sample well provides a measure of transmission or absorbance ($T=10^{-A}$). Obtaining a twofold increase in path length is especially important for high-density microplates, because smaller volumes imply shorter path lengths and hence lower sensitivity. The invention, which includes two passes through the sample, helps to increase the sensitivity in high-density low-volume wells. FIG. 16 shows results before and after correction using Equation 8.

For these experiments, one of the two spectral filters normally used for luminescence was removed, and the other filter was selected to match an absorbance band of interest of the sample. The refractive effects of the meniscus are minimized since they are reversed on the return trip after the light reflects off the bottom of the microplate well. In a preliminary experiment in a 96-well microplate, a 1.2 OD range was measured with about 0.1 OD resolution and acceptable linearity.

Figure 17:
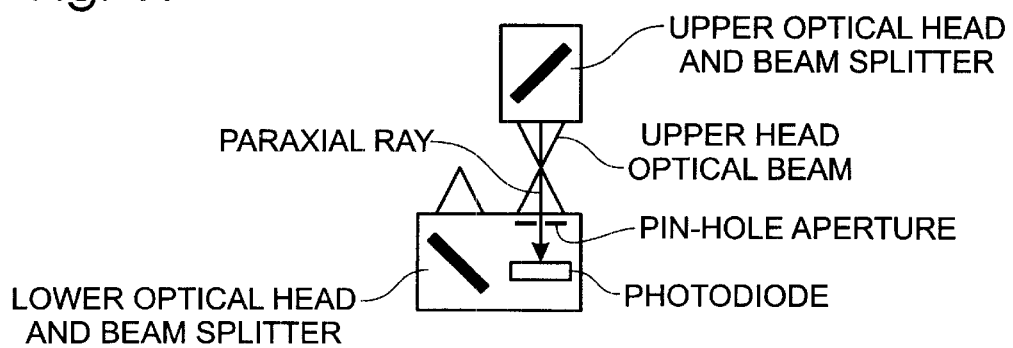
FIG. 17 is a schematic view of a system for measuring absorbance according to the invention.

FIG. 17 shows another system for measuring absorbance in a trans configuration according to the invention. In the disclosed embodiment described above, the detector takes the form of an upward-facing photodiode positioned directly below the optical axis of the upper head. A pin-hole aperture is disposed between the sample and the photodiode to limit the entry of light.

This system allows measurement of absorbance while luminescence or reflectance are measured by the optics in the upper head by the photomultiplier tube. The absorbance (or excitation) wavelength is selected using the excitation filter wheel. The reflectance or emission wavelength is selected using the emission filter wheel. A 50:50 beam splitter works well for absorbance/reflectance measurements, while a dichroic mirror may be more suitable from absorbance/luminescence measurements.

Measurement of absorbance in conjunction with other assays is useful in high-throughput screening. Abnormal absorbance measurements may indicate a quality-control problem, such as contamination or an air bubble. The absorbance data also could be used to detect or analyze false negatives or positives. It should be understood that the detector signal providing absorbance information may be processed to generate an actual absorbance value or may only be used to compute some quantity related to absorbance, such as a relative intensity of the signal.

An additional use for the design shown in FIG. 17 is to use the multi-mode measurement capabilities to determine location of reference fiducials on microplates, as described in U.S. patent application Ser. No. 09/156,318 and PCT Patent Application Serial No. PCT/US99/08410, both of which are incorporated herein by reference. For example, transmission or reflection measurements can be used to detect a hole or other such optically identifiable feature on the surface of a microplate. The location of the fiducial can be determined by scanning the microplate under the detector while continuously measuring the transmission and searching for a maximum or minimum. The XYZ stage coordinates are recorded at each fiducial. This provides the location of fiducials in stage coordinates. Since the positions of the fiducials are known relative to other features on the plate, any feature on the plate can be accurately found by determining an appropriate offset from the known fiducial location.

6. Scattering Assays

Figure 18:
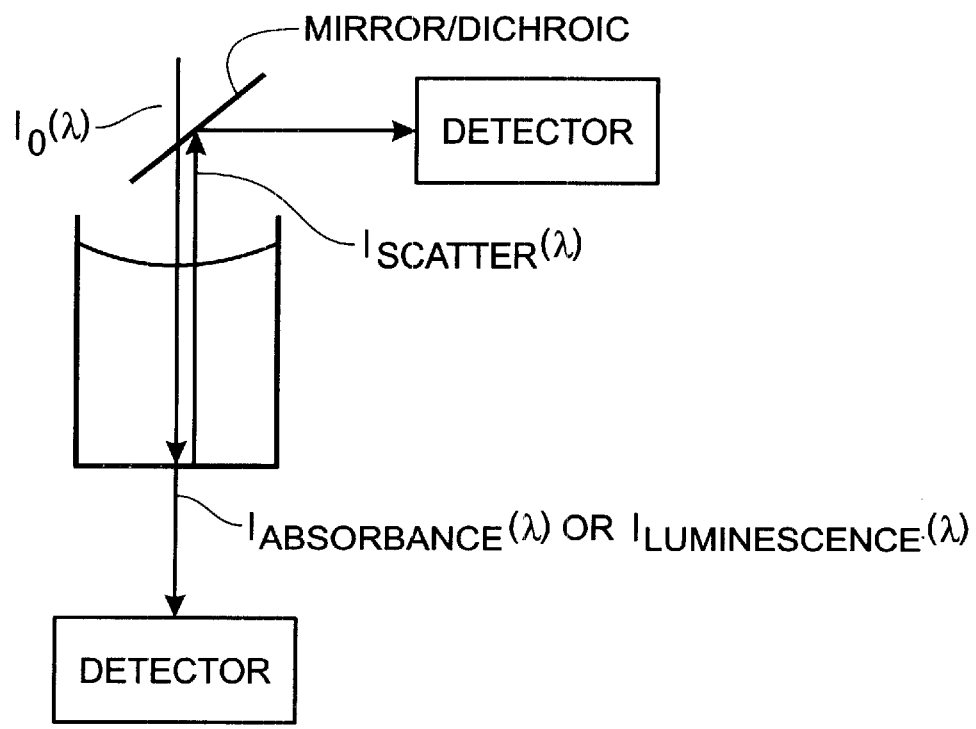
FIG. 18 is a schematic view of a system for measuring scattering according to the invention.

FIG. 18 schematically shows a scattering assay according to the invention in which scattered light is measured. Incident light $I_0$ is shone onto a sample. The sample includes a constituent that scatters the incident light. A component of the scattered light is received by a detector. The previously described technique of utilizing two polarizers also may be effective to reduce the effect of reflections on the scattering measurement. The best results for this type of scattering assay are obtained with a black or clear microplate that does not reflect or scatter significant amounts of the incident light.

A scattering assay according to the invention can be used alone or in conjunction with another spectroscopic assay. For example, the scattering assay can be conducted simultaneously with a luminescence assay to account for color quenching of the luminescence. In such a combined assay, the scattering is preferably monitored from the direction of the incident light as depicted in FIG. 18. Luminescence can be measured in either an epi- or trans-configuration as desired. This simultaneous measurement is facilitated by the wavelength (Stokes') shift of the luminescence relative to the incident (excitation) light, allowing separation of scattered and luminescence light.

It also is possible to conduct a combined scattering and absorbance assay. In a scattering/absorbance assay, the absorbance preferably is measured in the trans-direction, while the scattering preferably is measured in the epi-direction. It also is possible to conduct simultaneous scattering, luminescence and absorbance measurements by combining the scattering/absorbance, and scattering/luminescence assays. Moreover, it is also possible to conduct combined assays sequentially. In the case of sequential assays, it is possible to utilize the same detector for two or more types of measurements, such as scattering and luminescence.

Use of combined assays permits monitoring for various properties of the sample. Absorbance or scattering measurements outside a given range may indicate some problem with the sample, as described above. For example, an increase in scattering levels during a luminescence experiment can signal that a precipitate has formed in the sample, as might occur in a dilution series. Formation of a precipitate may decrease the luminescence signal. Without the scattering measurement, such a decrease might be falsely interpreted as a real decrease in the luminescence of the sample.

Although the invention has been disclosed in its preferred forms, the specific embodiments thereof as disclosed and illustrated herein are not to be considered in a limiting sense, because numerous variations are possible. Applicants regard the subject matter of their invention to include all novel and nonobvious combinations and subcombinations of the various elements, features, functions, and/or properties disclosed herein. No single feature, function, element or property of the disclosed embodiments is essential. For example, a reflective surface could be used in an absorbance assay in which light passes through one or more walls of the sample container, or single-pass illumination could be used in which light passes through an open side of the sample container. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope to the original claims, also are regarded as included within the subject matter of applicants' invention.

We claim:

1. A method of measuring absorbance of a sample, comprising:
   directing incident light from a light source to a measurement region;
   sequentially positioning each of a series of samples in the measurement region so that the incident light passes through each of the samples in a first direction, and for each of the samples:
      reflecting the incident light back through the sample in a second direction generally opposed to the first direction;
      receiving the reflected light; and
      computing a quantity related to the absorbance of the sample based on the amount of reflected light received.

2. The method of claim 1 further comprising the step of placing the samples in a corresponding series of sample wells in a sample plate.

3. The method of claim 2, wherein the sample wells in the sample plate have a surface that scatters light.

4. The method of claim 1 further comprising, for each of the samples, measuring luminescence of the sample while the sample is positioned in the measurement region.

5. The method of claim 1 further comprising separating light transmitted from the sample into a luminescence component and a reflected component.

6. A method for performing a spectroscopic assay, wherein a plurality of samples are automatically and sequentially placed into a measurement region, comprising for each sample:
   directing light from a light source onto the sample from a first side;
   detecting a first fraction of the incident light that passes through the sample to a second side without absorbance or scattering; and
   simultaneously detecting a second fraction of light transmitted from the sample on the first side generally opposite the direction of the incident light.

7. The method of claim 6, wherein the second fraction of light is luminescence light.

8. The method of claim 6, wherein the second fraction of light is scattered light.

9. The method of claim 6, wherein one of the samples is a blank for calibration.

10. The method of claim 9, wherein the blank sample is opaque.

11. The method of claim 10 further comprising the step of detecting the first fraction with the blank and using the detected value to compensate for background absorbance signal in subsequent samples.

12. The method of claim 6 further comprising passing the incident light through a first polarizer.

13. The method of claim 12 further comprising:
passing the second fraction of light through a second polarizer; and
orienting the second polarizer to reduce an undesired contribution to the signal.

14. The method of claim 13, wherein the second polarizer is oriented generally transverse to the first polarizer.

15. The method of claim 13, wherein the second polarizer is oriented generally parallel to the first polarizer.

16. A method of measuring luminescence, comprising:
providing a sample plate including a plurality of sample wells containing a corresponding plurality of samples;
positioning a first sample well for measurement;
illuminating the first sample well with incident light of a first wavelength, where light is transmitted from the sample as a result of illumination with incident light, the transmitted light including light at the first wavelength and light at a luminescence wavelength shifted from the first wavelength;
filtering at least part of the transmitted light from the sample to extract light at the luminescence wavelength;
detecting the extracted luminescence light; and
measuring transmitted light at the first wavelength.

17. The method of claim 16, wherein the steps of measuring and detecting are conducted simultaneously.

18. The method of claim 16, wherein the step of measuring is configured to detect scattered incident light.

19. The method of claim 16 further comprising the step of computing a quantity related to absorbance of the sample based on the measured transmitted light at the first wavelength.

20. The method of claim 19 further comprising utilizing the computed quantity related to absorbance to correct the detected luminescence to a level that would be detected without absorbance.

21. The method of claim 16, wherein the step of illuminating includes the substep of polarizing the incident light.

22. The method of claim 21, wherein the step of measuring includes the substep of passing the transmitted light through a polarizer prior to measuring.

23. The method of claim 16, wherein the sample wells in the sample plate have a surface that scatters incident light.

24. The method of claim 16 further comprising the step of placing a blank in one of the sample wells for use in calibrating the measurement obtained in step of measuring.

25. An apparatus for measuring absorbance, comprising:
a light source;
a sensor positioned to measure a quantity proportional to the amount of light output by the light source;
a system for directing light from the light source to a measurement region;
a stage configured to hold a plate containing a plurality of sample wells adapted to hold samples, the stage further being configured to place a selected one of the samples in the sample wells into the measurement region;
a reflector disposed to reflect light that has passed through a sample back through the sample as second time;
a detector configured to receive reflected light emitted from a sample well in the measurement region;
a processor adapted to compute an output based on the amount of reflected light received by the detector and based on the amount of light output by the light source.

26. A system for measuring absorbance, comprising:
a light source;
a stage configured to hold a plate containing a plurality of sample wells adapted to hold samples, the stage further being configured to place a selected one of the samples in the sample wells into a measurement region;
a detector; and
an optical system adapted to direct light in a path from the light source through the sample at least twice and then to the detector, wherein the majority of the light reaching the detector has passed at least twice through the sample.

27. The system of claim 26, wherein the optical system includes a reflective surface disposed on a bottom of the sample wells.

28. A system for measuring absorbance, comprising:
a light source;
a sample holder adapted to hold a sample in a measurement position, the sample holder having an open top and a reflective interior surface;
an optical system configured to deliver light from the light source to the open top into the sample; and
a detector positioned to receive primarily light reflected off the reflective interior surface.

29. The system of claim 28, wherein the sample holder is opaque to light from the light source.

30. The system of claim 28, wherein the sample holder is transparent to light from the light source with a scattering interior surface.

31. The system of claim 28 further including a filter disposed between the sample and the detector to block luminescence light preferentially to light from the light source.

32. The system of claim 28, wherein the optical system includes a polarizer disposed between the light source and the sample and a polarizer disposed between the sample and the detector.

33. An instrument for detecting light, comprising
a stage for holding a sample plate with a plurality of sample wells;
an upper optical head having an optical axis perpendicular to the stage configured for epi-style light detection from a sample contained in a selected one of the sample wells in the sample plate on the stage; and
a lower optical head including a light detector configured for trans-style light detection through a bottom of the selected sample well, wherein the light detection in the lower optical head is positioned directly along the optical axis below the stage.

34. The instrument of claim 33 wherein the light detector is a photodiode.

* * * * *